United States Patent
Maul et al.

(10) Patent No.: US 10,238,755 B2
(45) Date of Patent: Mar. 26, 2019

(54) METHODS AND COMPOSITIONS FOR REGULATION OF CELL AGING, CARCINOGENESIS AND REPROGRAMMING

(71) Applicant: The Wistar Institute of Anatomy and Biology, Philadelphia, PA (US)

(72) Inventors: Gerd G. Maul, Wynnewood, PA (US); Dmitri G. Negorev, West Chester, PA (US); Louise C. Showe, Media, PA (US); Olga V. Vladimirova, Philadelphia, PA (US)

(73) Assignee: The Wistar Institute of Anatomy and Biology, Philadelphia, PA (US)

( * ) Notice: Subject to any disclaimer, the term of this patent is extended or adjusted under 35 U.S.C. 154(b) by 36 days.

(21) Appl. No.: 14/361,970

(22) PCT Filed: Nov. 29, 2012

(86) PCT No.: PCT/US2012/067034
§ 371 (c)(1),
(2) Date: May 30, 2014

(87) PCT Pub. No.: WO2013/082268
PCT Pub. Date: Jun. 6, 2013

(65) Prior Publication Data
US 2014/0308255 A1    Oct. 16, 2014

Related U.S. Application Data

(60) Provisional application No. 61/565,298, filed on Nov. 30, 2011.

(51) Int. Cl.
| | |
|---|---|
| *C12N 5/00* | (2006.01) |
| *C12N 5/02* | (2006.01) |
| *C12N 15/63* | (2006.01) |
| *C07H 21/04* | (2006.01) |
| *A61K 48/00* | (2006.01) |
| *A61K 35/545* | (2015.01) |
| *C12N 5/074* | (2010.01) |
| *C12N 5/077* | (2010.01) |
| *C12N 15/113* | (2010.01) |

(52) U.S. Cl.
CPC .......... *A61K 48/005* (2013.01); *A61K 35/545* (2013.01); *C12N 5/0696* (2013.01); *C07H 21/04* (2013.01); *C12N 5/0656* (2013.01); *C12N 15/113* (2013.01); *C12N 15/63* (2013.01); *C12N 2501/998* (2013.01); *C12N 2506/1307* (2013.01); *C12N 2510/00* (2013.01); *C12N 2510/04* (2013.01); *C12N 2740/15041* (2013.01)

(58) Field of Classification Search
CPC .... C12N 5/0656; C12N 15/63; C12N 15/113; C12N 2506/1307; C12N 2510/00; C12N 2510/04; C07H 21/04

USPC ......... 435/375, 377, 455; 536/24.5
See application file for complete search history.

(56) References Cited

U.S. PATENT DOCUMENTS

| | | |
|---|---|---|
| 2008/0233610 A1 | 9/2008 | Thomson |
| 2010/0184033 A1 | 7/2010 | West |

FOREIGN PATENT DOCUMENTS

WO    WO-2012/054896    4/2012

OTHER PUBLICATIONS

Chapman et al., 2014, US 20140154691, effective filed Jun. 22, 2011.*
Negorev et al., 2006, Journal of Virology, vol. 80, No. 16, p. 8019-8029.*
Allegrucci et al., 2006, Human Reproduction Update, vol. Advance Access published on Aug. 26, 2006, p. 1-18.*
Zhao et al., 2012, Molecules, vol. 17, p. 6196-6236.*
Kolf et al., 2007, Arthritis Research & Therapy, vol. 9, p. 204, 10 pages.*
Alenzi et al., 2011, African Journal of Biotechnology, vol. 10(86), pp. 19929-19940.*
Bellin et al., 2012, Nature reviews/Molecular Cell Biology, vol. 13, p. 713-726.*
Li et al., 2014, Journal of Hematology & Oncology, 7:50, p. 1-18.*
Adler et al., Jul. 2011, Journal of General Virology, vol. 92, p. 1532-1538.*
Chapman et al., 2014, US 20140154691 A1, effective filed, Jun. 22, 2011.*

(Continued)

*Primary Examiner* — Shin Lin Chen
(74) *Attorney, Agent, or Firm* — Howson & Howson LLP; Colleen Schaller

(57) ABSTRACT

Compositions and methods described herein include somatic cells that are competent for reprogramming and malignant transformation and are characterized by a reduction of the levels of Sp100 in the cells, cells having markers of pluripotent stem cells, and methods for preparing same. Methods for reversibly regulating aging or reprogramming to pluripotency in a somatic cell involve modulating the expression of Sp100 therein. Methods and compositions for retarding the growth of or suppressing unwanted cell proliferation involve expressing, inducing expression of, or upregulating, Sp100 in a targeted cell that is undergoing unrestricted proliferation or replication or increasing exposure to Sp100 in the environment or microenvironment of the targeted cell. Also disclosed are methods for treating a proliferative disease or condition by increasing expression or levels of Sp100 in the targeted cell or its environment.

4 Claims, 4 Drawing Sheets
Specification includes a Sequence Listing.

(56) References Cited

OTHER PUBLICATIONS

Dahl et al., Jun. 2011, US 20110143436 A1, effective filed, Dec. 7, 2009.*
Hahn, W.C., Weinberg, R.A., Rules for Making Human Tumor Cells, New England Journal of Medicine, Nov. 2002, 347(20):1593-1603.
Lloyd, A., Limits to Lifespan, Natural Cell Biology, Feb. 2002, 4(2): E25-E27.
Dyck, J. et al., A Novel Macromolecular Structure is a Target of the Promyelocyte-Retinoic Acid Receptor Oncoprotein, Cell, Jan. 1994, 76(2): 333-343.
De Stanchina, E. et al., PML is a direct p53 target that modulates p53 effector functions, Molecular Cell, Feb. 2004, 13(4): 523-535.
Pearson, M. et al., PML regulates p53 acetylation and premature senescence induced by oncogenic Ras, Nature, Jul. 2000, 406(6792): 207-210.
Weichenhan, D. et al., , Evolution by fusion and amplification: the murine Sp100-rs gene cluster, Cytogenics and Cell Genetics, Jan. 1998, 80(1-4): 226-231.
Livak, K., T.D. Schmittgen,Analysis of relative gene expression data using real-time quantitative PCR and the 2(-delta delta C(T)) Method, Methods, Dec. 2001, 25(4): 402-408.
Gibson, T. et al., The APECED polyglandular autoimmune syndrome protein, AIRE-1, contains the SAND domain and is probably a transcription factor, Trends in Biochemical Sciences, Jul. 1998, 23(7): 242-244.
Steward, S.A. et al., Erosion of the telomeric single-strand overhang at replicative senescence, Nature Genetics, Apr. 2003, 33(4): 492-496.
Mathon, N.F., A.C. Lloyd, Cell senescence and cancer, Nature Reviews Cancer, Dec. 2001, 1(3): 203-211.
Hahn, W.C. et al., Creation of human tumour cells with defined genetic elements, Nature, Jul. 1999, 400(6743): 464-468.
Bodnar, A.G. et al., Extension of life-span by introduction of telomerase into normal human cells, Science, Jan. 1998, 279(5349): 349-352.
Okita, K. et al., Generation of germline-competent induced pluripotent stem cells, Nature, Jul. 2007, 448(7151): 313-317.
Wernig, M. et al., In vitro reprogramming of fibroblasts into a pluripotent ES-cell-like state, Nature, Jul. 2007, 448(7151): 318-324.
Boyer, B., J.P. Thiery., Epithelial cell adhesion mechanisms, Journal of Membrane Biology, Dec. 1989, 112(2): 97-108.
Zeisberg, M. et al., BMP-7 counteracts TGF-β1-induced epithelial-to-mesenchymal transition and reverses chronic renal injury, Nature Medicine, Jul. 2003, 9(7): 964-968.
Bottomley, M.J. et al., The SAND domain structure defines a novel DNA-binding fold in transcriptional regulation, Nature Structural and Molecular Biology, Jul. 2001, 8(7): 626-633.
Gazin, An elaborate pathway required for Ras-mediated epigenetic silencing, Nature, 449(7165):1073-7, Oct. 25, 2007.
Bissell, Putting tumours in context, Nature Reviews Cancer, 1(1):46-54, Oct. 2001.
Bavik, The gene expression program of prostate fibroblast senescence modulates neoplastic epithelial cell proliferation through paracrine mechanisms. Cancer Research, 66(2):794-802, Jan. 15, 2006.
Krtolica, Senescent fibroblasts promote epithelial cell growth and tumorigenesis: a link between cancer and aging, Proceedings of the National Academy of Sciences USA, 98(21):12072-7, Oct. 9, 2001.
Coppe, Senescence-associated secretory phenotypes reveal cell-nonautonomous functions of oncogenic RAS and the p53 tumor suppressor, PLoS Biol, 6(12):2853-68, Dec. 2, 2008.
Ascoli, Identification of a novel nuclear domain, Journal of Cell Biology, 112(5):785-95, Mar. 1991.
Ishov, PML is critical for ND10 formation and recruits the PML-interacting protein Daxx to this nuclear structure when modified by SUMO-1, Journal of Cell Biology, 147(2):221-34, Oct. 18, 1999.
Cohen, PML RING suppresses oncogenic transformation by reducing the affinity of eIF4E for mRNA, EMBO J, 20(16):4547-59, Aug. 15, 2001.
Mu, PML, a growth suppressor disrupted in acute promyelocytic leukemia, Molecular and Cellular Biology, 14(10):6858-67, Oct. 1994.
Regio, Role of promyelocytic leukemia (PML) protein in tumor suppression, Journal of Experimental Medicine, 193(4):521-29, Feb. 19, 2001.
Negorev, Differential role of Sp100 isoforms in interferon-mediated repression of herpes simplex virus type 1 immediate-early protein expression, Journal of Virology, 80(16):8019-29, Aug. 2006.
Negorev, Differential functions of interferon-upregulated Sp100 isoforms: herpes simplex virus type 1 promoter-based immediate-early gene suppression and PML protection from ICP0-mediated degradation, Journal of Virology, 83(10):5168-80, May 2009.
Nasr, Therapy-induced PML/RARA proteolysis and acute promyelocytic leukemia cure. Clinical Cancer Research, 15(20):6321-6, Oct. 15, 2009.
Ferbeyre, PML is induced by oncogenic ras and promotes premature senescence, Genes and Development, 14(16):2015-27, Aug. 15, 2000.
Everett, PML contributes to a cellular mechanism of repression of herpes simplex virus type 1 infection that is inactivated by ICP0, Journal of Virology, 80(16):7995-8005, Aug. 2006.
Tavalai, Evidence for a role of the cellular ND10 protein PML in mediating intrinsic immunity against human cytomegalovirus infections, Journal of Virology, 80(16):8006-18, Aug. 2006.
Guldner, Splice variants of the nuclear dot-associated Sp100 protein contain homologies to HMG-1 and a human nuclear phosphoprotein-box motif, Journal of Cell Science, 112(Pt 5):733-47, Mar. 1999.
Everett, Replication of ICP0-null mutant herpes simplex virus type 1 is restricted by both PML and Sp100, Journal of Virology, 82(6):2661-72, Mar. 2008.
Ishov, Heterochromatin and ND10 are cell-cycle regulated and phosphorylation-dependent alternate nuclear sites of the transcription repressor Daxx and SWI/SNF protein ATRX, Journal of Cell Science, 117(Pt 17):3807-20, Aug. 1, 2004, e-publication: Jul. 13, 2004.
Storey, Statistical significance for genomewide studies, Proceedings of the National Academy of Sciences USA, 100(16):9440-5, Aug. 5, 2003, e-publication: Jul. 25, 2003.
Bischof, Deconstructing PML-induced premature senescence, EMBO J, 21(13):3358-69, Jul. 1, 2002.
Rogakou, DNA double-stranded breaks induce histone H2AX phosphorylation on serine 139. Journal of Biological Chemistry, 273(10):5858-68, Mar. 6, 1998.
Park, Newcastle disease virus V protein is a determinant of host range restriction. Journal of Virology, 77(17):9522-32, Sep. 2003.
Chandriani, A core MYC gene expression signature is prominent in basal-like breast cancer but only partially overlaps the core serum response, PLoS One, 4(8):e6693, Aug. 19, 2009.
Chang, Lin-28B transactivation is necessary for Myc-mediated let-7 repression and proliferation, Proceedings of the National Academy of Sciences USA, 106(9):3384-9, Mar. 3, 2009, e-publication: Feb. 11, 2009.
Viswanathan, Lin28 promotes transformation and is associated with advanced human malignancies, Nature Genetics, 41(7):843-8, Jul. 2009, e-publication: May 31, 2009.
Jeong, LIN28B confers radio-resistance through the post-transcriptional control of KRAS, Experimental and Molecular Medicine, 41(12):912-8, Dec. 31, 2009.
Chang, A genomic strategy to elucidate modules of oncogenic pathway signaling networks, Molecular Cell, 34(1):104-14, Apr. 10, 2009.
Esteller, Inactivation of the DNA repair gene $O^6$-methylguanine-DNA methyltransferase by promoter hypermethylation is associated with G to A mutations in K-ras in colorectal tumorigenesis, Cancer Research, 60(9):2368-71, May 1, 2000.
Wong, Module map of stem cell genes guides creation of epithelial cancer stem cells, Cell Stem Cell, 2(4):333-44, Apr. 10, 2008.

(56) References Cited

OTHER PUBLICATIONS

Yu, Induced pluripotent stem cell lines derived from human somatic cells, Science, 318(5858)1917-20, Dec. 21, 2007, e-publication: Nov. 20, 2007.
Samavarchi-Tehrani, Functional genomics reveals a BMP-driven mesenchymal-to-epithelial transition in the initiation of somatic cell reprogramming, Cell Stem Cell, 7(1):64-77, Jul. 2010, e-publication: Jun. 17, 2010.
Li, A mesenchymal-to-epithelial transition initiates and is required for the nuclear reprogramming of mouse fibroblasts, Cell Stem Cell, 7(1):51-63, Jul. 2, 2010, e-publication: Jun. 17, 2010.
Lehming, Chromatin components as part of a putative transcriptional repressing complex, Proceedings of the National Academy of Sciences USA, 95(13):7322-6, Jun. 23, 1998.
Bea, Uniparental disomies, homozygous deletions, amplifications, and target genes in mantle cell lymphoma revealed by integrative high-resolution whole-genome profiling, Blood, 113(13):3059-69, Mar. 26, 2009, e-publication: Nov. 4, 2008.
Takahashi, Induction of pluripotent stem cells from adult human fibroblasts by defined factors, Cell, 131(5):861-72, Nov. 30, 2007.
Negorev, Sp100 as a potent tumor suppressor: accelerated senescence and rapid malignant transformation of human fibroblasts through modulation of an embryonic stem cell program, Cancer Research, 70(23): 9991-10001, Dec. 1, 2010.
Tavalai, Evidence for dual antiviral role of the major nuclear domain 10 component Sp100 during the immediate-early and late phases of the human cytomegalovirus replication cycle, Journal of Virology, 85(18):9447-9458, Sep. 2011.
Adler, Human Cytomegalovirus immediate-early gene expression is restricted by the nuclear domain 10 component Sp100, Journal of General Virology, 92:1532-1538, Jul. 2011, e-publication: Apr. 6, 2011.
Newhart, Sp100A promotes chromatin decondensation at a cytomegalovirus-promoter-regulated transcription site, Molecular Biology of the Cell, 24(9):1454-1468, May 2013.
International Search Report and Written Opinion dated Feb. 15, 2013.
International Preliminary Examination Report dated Jun. 12, 2014.
Negorev et al., "Retraction: Sp100 as a Potent Tumor Suppressor: Accelerated Senescence and Rapid Malignant Transformation of Human Fibroblasts through Modulation of an Embryonic Stem Cell Program", Cancer Res., vol. 73(15)4960-1, Aug. 2013, includes retracted paper.

\* cited by examiner

SEQUENCE LISTING

```
<160> NUMBER OF SEQ ID NOS: 42

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
cctcctcagc caaagaagtg                                             20

<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
gtggtgatgt acagccatgc                                             20

<210> SEQ ID NO 3
<211> LENGTH: 20
<212> TYPE: DNA
<213> ORGANISM: Artificial Sequence
```

<220> FEATURE:
<223> OTHER INFORMATION: primer

<400> SEQUENCE: 3
cttctctgta cccatacagc                                               20

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
caggtagata agcctccaag                                               20

<210> SEQ ID NO 5
<211> LENGTH: 22
<212> TYPE: DNA
<213> ORGANISM: Artificial Sequence
<220> FEATURE:
<223> OTHER INFORMATION: primer

<400> SEQUENCE: 5
tggtccgagt gtggttctgt aa                                            22

<210> SEQ ID NO 6
<211> LENGTH: 21
<212> TYPE: DNA
<213> ORGANISM: Artificial Sequence
<220> FEATURE:
<223> OTHER INFORMATION: primer

<400> SEQUENCE: 6
tgtgcatagt cgctgcttga t                                             21

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
gccggctctt caccatcccg                                               20

<210> SEQ ID NO 8
<211> LENGTH: 23
<212> TYPE: DNA
<213> ORGANISM: Artificial Sequence
<220> FEATURE:
<223> OTHER INFORMATION: primer

<400> SEQUENCE: 8
gctgcagacc actctgtggc acg                                           23

<210> SEQ ID NO 9
<211> LENGTH: 16
<212> TYPE: DNA
<213> ORGANISM: Artificial Sequence
<220> FEATURE:
<223> OTHER INFORMATION: primer

<400> SEQUENCE: 9
gcagctcgga agactc                                                   16

```
<210> SEQ ID NO 10
<211> LENGTH: 16
<212> TYPE: DNA
<213> ORGANISM: Artificial Sequence
<220> FEATURE:
<223> OTHER INFORMATION: primer

<400> SEQUENCE: 10
gtagccccag gagaac                                                      16

<210> SEQ ID NO 11
<211> LENGTH: 22
<212> TYPE: DNA
<213> ORGANISM: Artificial Sequence
<220> FEATURE:
<223> OTHER INFORMATION: primer

<400> SEQUENCE: 11
cggcggctgc aggaaaagga gt                                               22

<210> SEQ ID NO 12
<211> LENGTH: 19
<212> TYPE: DNA
<213> ORGANISM: Artificial Sequence
<220> FEATURE:
<223> OTHER INFORMATION: primer

<400> SEQUENCE: 12
gcgccgggcc aacacagga                                                   19

<210> SEQ ID NO 13
<211> LENGTH: 21
<212> TYPE: DNA
<213> ORGANISM: Artificial Sequence
<220> FEATURE:
<223> OTHER INFORMATION: primer

<400> SEQUENCE: 13
cgtctccaca catcagcaca a                                                21

<210> SEQ ID NO 14
<211> LENGTH: 20
<212> TYPE: DNA
<213> ORGANISM: Artificial Sequence
<220> FEATURE:
<223> OTHER INFORMATION: primer

<400> SEQUENCE: 14
ttggcagcag gatagtcctt                                                  20

<210> SEQ ID NO 15
<211> LENGTH: 19
<212> TYPE: DNA
<213> ORGANISM: Artificial Sequence
<220> FEATURE:
<223> OTHER INFORMATION: primer

<400> SEQUENCE: 15
gttttgagga agtgctgag                                                   19

<210> SEQ ID NO 16
<211> LENGTH: 20
<212> TYPE: DNA
<213> ORGANISM: Artificial Sequence
<220> FEATURE:
<223> OTHER INFORMATION: primer
```

<400> SEQUENCE: 16
cagtcacagt ggtaaggttt                                         20

<210> SEQ ID NO 17
<211> LENGTH: 26
<212> TYPE: DNA
<213> ORGANISM: Artificial Sequence
<220> FEATURE:
<223> OTHER INFORMATION: primer

<400> SEQUENCE: 17
gggaaatggg aggggtgcaa aagagg                                  26

<210> SEQ ID NO 18
<211> LENGTH: 26
<212> TYPE: DNA
<213> ORGANISM: Artificial Sequence
<220> FEATURE:
<223> OTHER INFORMATION: primer

<400> SEQUENCE: 18
ttgcgtgagt gtggatggga ttggtg                                  26

<210> SEQ ID NO 19
<211> LENGTH: 20
<212> TYPE: DNA
<213> ORGANISM: Artificial Sequence
<220> FEATURE:
<223> OTHER INFORMATION: primer

<400> SEQUENCE: 19
tgggaactcc tttttgcatt                                         20

<210> SEQ ID NO 20
<211> LENGTH: 21
<212> TYPE: DNA
<213> ORGANISM: Artificial Sequence
<220> FEATURE:
<223> OTHER INFORMATION: primer

<400> SEQUENCE: 20
caaacgacaa tgatgtcaac c                                       21

<210> SEQ ID NO 21
<211> LENGTH: 20
<212> TYPE: DNA
<213> ORGANISM: Artificial Sequence
<220> FEATURE:
<223> OTHER INFORMATION: primer

<400> SEQUENCE: 21
aggagcgatt caaacaagga                                         20

<210> SEQ ID NO 22
<211> LENGTH: 20
<212> TYPE: DNA
<213> ORGANISM: Artificial Sequence
<220> FEATURE:
<223> OTHER INFORMATION: primer

<400> SEQUENCE: 22
agacgagaca ttggcagaag                                         20

<210> SEQ ID NO 23

```
<211> LENGTH: 20
<212> TYPE: DNA
<213> ORGANISM: Artificial Sequence
<220> FEATURE:
<223> OTHER INFORMATION: primer

<400> SEQUENCE: 23
aagccaatca ggtcatcagg                                                 20

<210> SEQ ID NO 24
<211> LENGTH: 20
<212> TYPE: DNA
<213> ORGANISM: Artificial Sequence
<220> FEATURE:
<223> OTHER INFORMATION: primer

<400> SEQUENCE: 24
atgtcctgca caaacccttc                                                 20

<210> SEQ ID NO 25
<211> LENGTH: 20
<212> TYPE: DNA
<213> ORGANISM: Artificial Sequence
<220> FEATURE:
<223> OTHER INFORMATION: primer

<400> SEQUENCE: 25
tagccctgtc ctggtggtat                                                 20

<210> SEQ ID NO 26
<211> LENGTH: 20
<212> TYPE: DNA
<213> ORGANISM: Artificial Sequence
<220> FEATURE:
<223> OTHER INFORMATION: primer

<400> SEQUENCE: 26
tgtcaacaaa acagctgcaa                                                 20

<210> SEQ ID NO 27
<211> LENGTH: 20
<212> TYPE: DNA
<213> ORGANISM: Artificial Sequence
<220> FEATURE:
<223> OTHER INFORMATION: primer

<400> SEQUENCE: 27
cggaagagtg tctggagcaa                                                 20

<210> SEQ ID NO 28
<211> LENGTH: 19
<212> TYPE: DNA
<213> ORGANISM: Artificial Sequence
<220> FEATURE:
<223> OTHER INFORMATION: primer

<400> SEQUENCE: 28
ggatgaagcg gagtctgga                                                  19

<210> SEQ ID NO 29
<211> LENGTH: 22
<212> TYPE: DNA
<213> ORGANISM: Artificial Sequence
<220> FEATURE:
<223> OTHER INFORMATION: primer

<400> SEQUENCE: 29
```

```
caggtgatca acgacggaga ca                                              22

<210> SEQ ID NO 30
<211> LENGTH: 22
<212> TYPE: DNA
<213> ORGANISM: Artificial Sequence
<220> FEATURE:
<223> OTHER INFORMATION: primer

<400> SEQUENCE: 30
gtcgatcgtc aggatggaca cg                                              22

<210> SEQ ID NO 31
<211> LENGTH: 20
<212> TYPE: DNA
<213> ORGANISM: Artificial Sequence
<220> FEATURE:
<223> OTHER INFORMATION: primer

<400> SEQUENCE: 31
caaaggcaaa caacccactt                                                 20

<210> SEQ ID NO 32
<211> LENGTH: 20
<212> TYPE: DNA
<213> ORGANISM: Artificial Sequence
<220> FEATURE:
<223> OTHER INFORMATION: primer

<400> SEQUENCE: 32
tctgctggag gctgaggtat                                                 20

<210> SEQ ID NO 33
<211> LENGTH: 20
<212> TYPE: DNA
<213> ORGANISM: Artificial Sequence
<220> FEATURE:
<223> OTHER INFORMATION: primer

<400> SEQUENCE: 33
aggcctgctg aaaatgactg                                                 20

<210> SEQ ID NO 34
<211> LENGTH: 20
<212> TYPE: DNA
<213> ORGANISM: Artificial Sequence
<220> FEATURE:
<223> OTHER INFORMATION: primer

<400> SEQUENCE: 34
tacacaaaga aagccctccc                                                 20

<210> SEQ ID NO 35
<211> LENGTH: 22
<212> TYPE: DNA
<213> ORGANISM: Artificial Sequence
<220> FEATURE:
<223> OTHER INFORMATION: primer

<400> SEQUENCE: 35
acgcttcgac aatgagacgt tc                                              22

<210> SEQ ID NO 36
<211> LENGTH: 22
<212> TYPE: DNA
```

```
<213> ORGANISM: Artificial Sequence
<220> FEATURE:
<223> OTHER INFORMATION: primer

<400> SEQUENCE: 36
tggcgttcat gtaggagttc ag                                              22

<210> SEQ ID NO 37
<211> LENGTH: 21
<212> TYPE: DNA
<213> ORGANISM: Artificial Sequence
<220> FEATURE:
<223> OTHER INFORMATION: primer

<400> SEQUENCE: 37
gaacgcattg ccacatacac t                                               21

<210> SEQ ID NO 38
<211> LENGTH: 21
<212> TYPE: DNA
<213> ORGANISM: Artificial Sequence
<220> FEATURE:
<223> OTHER INFORMATION: primer

<400> SEQUENCE: 38
ctgtggaggt ggtgagagag a                                               21

<210> SEQ ID NO 39
<211> LENGTH: 24
<212> TYPE: DNA
<213> ORGANISM: Artificial Sequence
<220> FEATURE:
<223> OTHER INFORMATION: primer

<400> SEQUENCE: 39
aggaaggacc tctatgctaa caat                                            24

<210> SEQ ID NO 40
<211> LENGTH: 24
<212> TYPE: DNA
<213> ORGANISM: Artificial Sequence
<220> FEATURE:
<223> OTHER INFORMATION: primer

<400> SEQUENCE: 40
aacacatagg taacgagtca gagc                                            24

<210> SEQ ID NO 41
<211> LENGTH: 21
<212> TYPE: DNA
<213> ORGANISM: Artificial Sequence
<220> FEATURE:
<223> OTHER INFORMATION: primer

<400> SEQUENCE: 41
ctgggctaca ctgagcacca g                                               21

<210> SEQ ID NO 42
<211> LENGTH: 18
<212> TYPE: DNA
<213> ORGANISM: Artificial Sequence
```

```
<220> FEATURE:
<223> OTHER INFORMATION: primer

<400> SEQUENCE: 42
ccagcgtcaa aggtggag                                              18
```

METHODS AND COMPOSITIONS FOR REGULATION OF CELL AGING, CARCINOGENESIS AND REPROGRAMMING

CROSS-REFERENCE TO RELATED APPLICATIONS

This application is a national stage of International Patent Application No. PCT/US2012/067034, filed Nov. 29, 2012, which claims the benefit of the priority of US Provisional Patent Application No. 61/565,298, filed Nov. 30, 2011, which applications are incorporated herein by reference.

STATEMENT REGARDING FEDERALLY SPONSORED RESEARCH OR DEVELOPMENT

This invention was made with government support under Grant Nos. R01 AI041136, GM057599, S10 RR024693 and R01 CA132098 awarded by the National Institutes of Health. The government has certain rights in this invention.

BACKGROUND OF THE INVENTION

The manipulation of replication characteristics and differentiated state of cells is an area of great interest for the development of cancer therapies, the field of tissue/organ transplantation and in the field of aging generally.

Normal cells typically divide for a highly restricted number of generations, and then enter a state of replicative senescence that can be characterized by acidic β-galactosidase staining, and in the case of many human cells, shortened telomeres leading to DNA damage checkpoint arrest. For example, normal human fibroblasts rarely if ever spontaneously immortalize in vitro. Senescent human fibroblasts have been demonstrated to have the capacity to both stimulate the proliferation of premalignant and malignant epithelial cells in culture, and to increase the tumorigenicity of premalignant epithelial cells in mouse xenografts. Thus, senescent human fibroblasts can create a tissue microenvironment that promotes multiple stages of tumor evolution through the senescence-associated secretory phenotype (SASP). This phenotype develops slowly and only after DNA damage, when senescent fibroblasts begin secreting IL-6, IL-8 and other cytokines that promote transformation of epithelial cells. In addition, said SASP is believed to play an important role in the aging of tissues by promoting the destruction of extracellular matrix, and triggering other age-related pathologies.

Similarly, normal cultured somatic cell types such as cultured human somatic cell types rarely if ever spontaneously transform to malignant cells capable of forming malignant tumors. Such transformation of normal somatic cells into malignant cells capable of forming malignant tumors generally requires the exogenous introduction of oncogenes, the abrogation of tumor suppressor genes, and the exogenous introduction of the catalytic component of telomerase.

In addition, normal cultured mammalian cells, such as those from humans rarely if ever spontaneously revert back to a state of pluripotency. This lack of competence for reprogramming leads to inefficiencies in transcriptional reprogramming by the exogenous addition of factors such as OCT4, SOX2, MYC, LIN28, KLF4, and NANOG.

There remains a need in the art for effective compositions and mechanisms that enable control of telomerase activity, the conversion of a normal cell to its malignant counterpart, and reprogramming of a normal cell to pluripotency to permit therapeutic treatment of diseases and conditions related to cell aging, screening and targets for the diagnosis and therapy for cancer, and to facilitate the reprogramming of somatic cells to pluripotency.

SUMMARY OF THE INVENTION

In one aspect, a composition of somatic cells competent for reprogramming to express pluripotency markers are provided, which are characterized by a reduction in the level or activity of Sp100 in the cells.

In another aspect, a composition of somatic cells competent for reprogramming are provided, which cells have markers of pluripotent stem cells. Such cells are prepared by serial propagation, or otherwise identifying subsets of the somatic cells made competent for reprogramming having reduced Sp100 levels as described herein.

In another aspect, a method of producing a somatic cell competent for reprogramming comprises down-regulating or reducing the expression level of Sp100, or otherwise interfering with the activity of Sp100, in a selected somatic cell. In one embodiment, this method further involves serially propagating the cells having reduced Sp100 levels to yield cells with markers of pluripotent stem cells.

In still another aspect, a method for reversably regulating aging or senescence in a somatic cell involves modulating the expression of Sp100 therein. In one embodiment, the expression of Sp100 is reduced in the cell, and the catalytic component of telomerase, also known as telomerase reverse transcriptase, (TERT) is reactivated, thereby retarding aging or senescence of the cell. In another embodiment, the expression of Sp100 is increased in the cell, thereby returning the cell to a replication limited stage.

In another aspect, a method for activating the expression of stem cell markers and stem cell pluripotency or function in a somatic cell involves down-regulating or reducing the expression level of Sp100, or otherwise interfering with the activity of Sp100, expressed in the somatic cells. In one embodiment, the resulting cells made competent for reprogramming to pluripotency are serially propagated in conditions that promote the growth of embryonic stem cell, or induced pluripotent stem cells, including but not limited to, FGF2-containing medium and growth on feeder cells.

In another aspect, a method for transitioning a replication limited somatic cell to an immortal cell involves down-regulating or reducing the expression level of Sp100, or otherwise interfering with the activity of Sp100, expressed in the somatic cells, and serially propagating the cells.

In still a further aspect, a method for retarding the unrestricted growth and relatively undifferentiated state of a neoplastic cell, e.g., a benign or malignant cell, comprises expressing, inducing expression of, or upregulating the activity of, Sp100 in the cell demonstrating unrestricted growth, in an anti-tumor T cell, or in the microenvironment of the cell demonstrating unrestricted growth, such as a benign or malignant cancer cell or tumor cell.

In another aspect, a method for treating a condition caused by unrestricted cell growth in a mammalian subject comprises administering to a subject in need thereof a therapeutic composition that expresses, induces expression of, or upregulates, the level or activity of Sp100 in the cell characterized by unrestricted growth (e.g., a benign or malignant neoplastic cell), or in an anti-tumor T cell, or in the microenvironment of in the cell characterized by unrestricted growth.

In another aspect, a pharmaceutical composition is provided that expresses, induces expression of, or upregulates, the level or activity of Sp100 in a cell. In one embodiment, the composition is a vector that expresses, induces expression of, or upregulates, the level of Sp100, in a cell.

In another aspect, a pharmaceutical composition comprises a cell transfected ex vivo with a vector that expresses, induces expression of, or upregulates, the level of Sp100, in a cell.

In another aspect, a method for screening for useful agents including but not limited to small molecules, aptomers, and siRNAs, that up or down-regulate the expression level of Sp100 or Sp100 activity to differentiate cancer cells or to make cells competent for reprogramming is provided.

In yet another aspect, a method and kits are provided for diagnosing a proliferative disease, condition or disorder by detecting or measuring the level or activity of Sp100 expression (as either nucleic acid or protein) in a cell.

Other aspects and advantages of these compositions and methods are described further in the following detailed description of the preferred embodiments thereof.

BRIEF DESCRIPTION OF THE DRAWINGS

FIG. 1A is a schematic presentation of Sp100 isoforms and location of target shRNAs (S2 and A7 for all Sp100 isoforms; A11 and B1 for SAND domain containing isoforms only).

FIG. 1B is a bar graph of data from a qPCR analysis of Sp100 isoforms expression in the BJ cell lines. Reduction of transcripts in BJ-S, total absence of Sp100 isoforms in BJsm, but retention of PML IV expression in BJV and BJ-S. High expression of PML VI mRNA in senescing BJ-SAND and in fast proliferating BJsm cells.

FIG. 1C are Western blotting analyses of Sp100, PML and Daxx proteins expression in the different BJ cell lines. Loss of Sp100 in BJ-S and BJsm. Loss of PML and Daxx proteins in BJsm.

FIG. 2A is a Western blot of different BJ cell types showing low or no p53 in BJV, BJ-S and BJ-SAND cells but activation of p53 expression in BJsm cells. Stripped membrane was reprobed and shows loss of p21CIP1 expression as well as MYC expression in BJsm cells.

FIG. 2B is a RT-PCR analysis of MYC and its downstream targets TERT and LIN28B expression in the BJ cell lines, the latter only expressed in BJsm cells.

FIG. 2C is a bar graph, and Western Blot showing the expression levels of these Sp100 isoforms and, using combined EZH2 and p53 antibodies, the presence of these proteins, where the nuclear EZH2 protein functions as the loading control.

FIG. 2D is a graph showing a comparison of p21CIP1 promoter driven reporter plasmids upon BJ cell cotransfection of Sp100A and p53.

FIG. 2E is a Venn diagram of significantly changed genes expression in BJsm cells in comparison with MYC-regulated and MYC core genes by overlapping gene expression data with those found in the literature. Diagram below represents the relationship between MYC and K-RAS expression.

FIG. 2F is a bar graph of qPCR analysis of micro-RNAs let-7a and let-7d expression. Both are suppressed in BJsm cells.

FIG. 2G is an RT-PCR of LIN28B, MGMT and KRAS.

FIG. 2H is a western blot of the KRAS oncogene. The KRAS protein is overexpressed in BJsm cells.

FIG. 3A is RT-PCR for ACTA2 and PAIL, showing that these genes are down regulated in BJsm cells and the indicator for epithelial cells, E-cadherin, is upregulated. BMP7, which functions as inhibitor of epithelial-mesenchymal transition (EMT), is also upregulated.

FIG. 3B is a Western blot showing upregulation of E-cadherin in BJsm cells and down regulation for vimentin and fibronectin, with tubulin as a loading control.

DETAILED DESCRIPTION OF THE INVENTION

Figure 1:
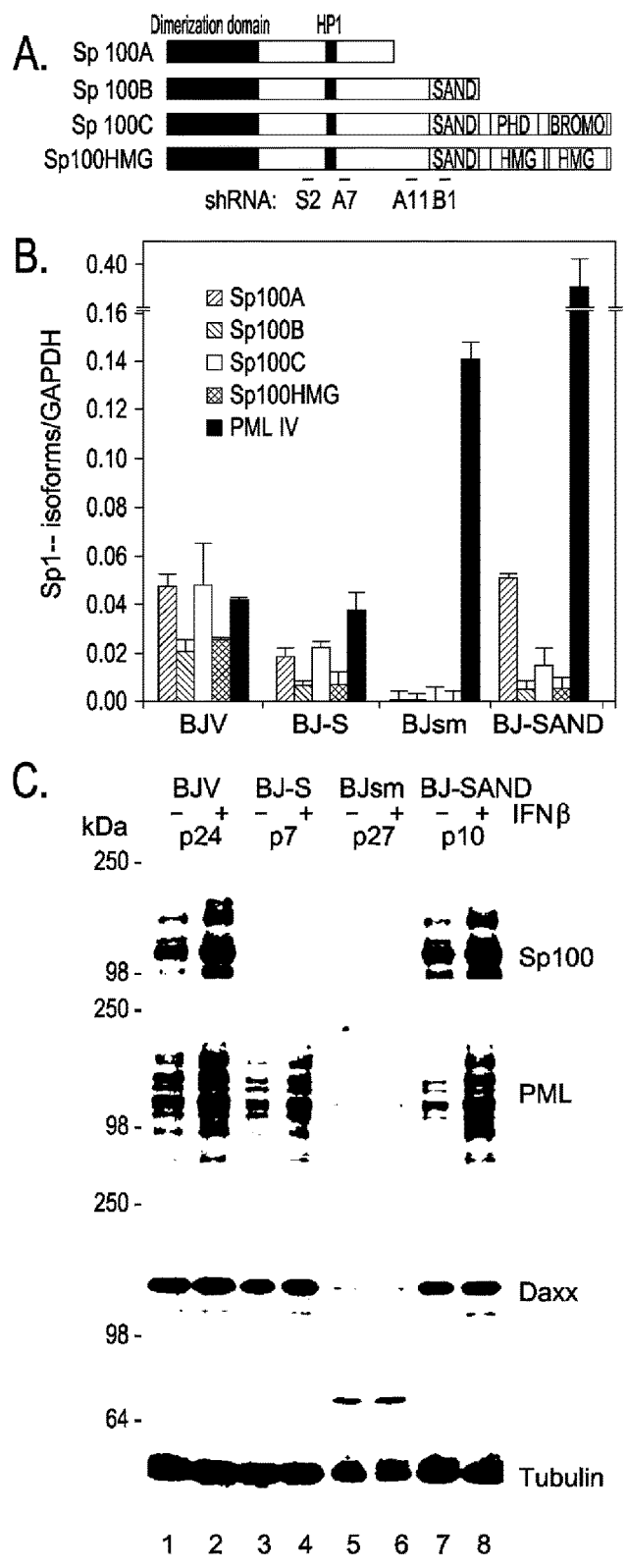
FIGS. 1A-1C provide data that show that complete loss of Sp100 immortalizes and transforms normal BJ foreskin fibroblasts.

The compositions and methods provided herein are based on the inventors' unexpected discovery that Sp100 isoforms are involved in the regulation of cell aging or senescence and that Sp100 behaves as a tumor suppressor. This discovery has led to methods and compositions useful in therapeutic or diagnostic treatment of patients and in drug development as provided below.

Patient" or "subject" as used herein means a multicellular and/or mammalian animal, including a human, a veterinary or farm animal, a domestic animal or pet, and animals normally used for clinical research. In one embodiment, the subject of these methods and compositions is a human. Still other suitable subjects include, without limitation, murine, rat, canine, feline, porcine, bovine, ovine, and others.

SP100 is a single-copy gene located on human chromosome 2q37 (Everett R D et al, 2006 J. Virol., 80(16):7995-8005), and produces five major alternatively spliced Sp100 protein isoforms, the mRNA and protein sequences of which are publically available as reported in Table 1.

TABLE 1

| Sp100 nuclear autoantigen isoform | mRNA sequence NCBI reference | Protein Sequence NCBI reference |
|---|---|---|
| Isoform 1; Sp100-C | NM_001080391.1 | NP_001073860.1 |
| Isoform 2; Sp100-HMG | NM_003113.3 | NP_003104.2 |
| Isoform 3; Sp100-B | NM_001206701.1 | NP_001193630.1 |
| Isoform 4; Sp100-A | NM_001206702.1 | NP_001193631.1 |
| Isoform 5 | NM_001206703.1 | NP_001193632.1 |
| Isoform 6 | NM_001206704.1 | NP_001193633.1 |

Sp100 is a prototypical protein of ND10/PML nuclear bodies, which colocalizes with Daxx and the proto-oncogenic PML. ND10 or PML nuclear bodies were originally identified using sera from patients with various auto-immune conditions. Three major proteins that associate with ND10 bodies are identified as PML (oncogene), DAXX (transcriptional repressor), and Sp100. These proteins had been shown to be induced by treatment with interferon and to play a role in facilitating the ability of interferon to regulate viral infections. Sp100 is upregulated by interferon (IFN) and is part of an intrinsic anti-viral defense mechanism. All isoforms share the 476 N-terminal amino acids with the most abundant isoform, Sp100A, aberrantly migrating at 100 kDa (Guldner H H et al, 1999 J Cell Sci, 112(Pt 5):733-47). The three minor isoforms contain a SAND domain, so named after Sp100, AIRE, NucP41/75 and DEAF1, transcriptional regulators that bind to DNA. A highly conserved tryptophan occurs at the DNA binding interface of the SAND domains of each of these proteins. An Sp100B variant, constructed with a mutation of this tryptophan (W655Q), loses its ability to repress transcription of HSV-1 virus as well as IFN-dependent suppression of viral gene expression (Negorev D G, et al, 2006 J Virol, 80(16): 8019-29; Negorev D G et al, 2009 J Virol, 83(10):5168-80). In addition to the SAND domain, the Sp100 isoforms contain PHD, Bromo and HMG domains and are highly sumoylated. These characteristics suggest a role for Sp100 in chromatin-mediated gene regulation.

The inventors unexpectedly found that when the level of the Sp100 protein was reduced, normal diploid fibroblasts rapidly senesce. Additionally a serendipitous observation was made when these cells remained in culture. The large normally flat cells began to change shape and small rapidly dividing cells began to appear in the cultures. The derivation of the small cells from the larger cells was confirmed by matching DNA fingerprints. While cultured human cells rarely, if ever, immortalize unless exogenous TERT is introduced, these small cells do not enter senescence but overcome the limit for the number of cell divisions that is normal for them (i.e. immortalize). Furthermore, in a characteristic that was found by the inventors to be surprising, and believed to be unique in the history of cancer research, these cells in which Sp100 was reduced or extinguished produced malignant tumors when injected into nude mice as demonstrated in the examples. This transformation is accompanied by the loss of ND10 nuclear bodies.

The data produced by the inventors provided evidence that reducing expression of just one gene converted a normal, replication limited diploid cell into an immortalized tumor cell. To the inventors' knowledge, this is the first time a single genetic modification of a human gene has been observed to lead to malignant transformation. A reintroduction of one Sp100 isoform, Sp100-A, is sufficient to prevent the emergence of the highly tumorigenic cells and reinstate the pathway to senescence. An additional observation indicated that the transition from replication limited to immortal cells activates a transient phase characterized by the expression of pluripotent stem cell markers such as POU5F1 (OCT4), TERT, SOX2, NANOG, and CDH1 (E-Cadherin). The senescent program can be stopped, redirected and even reversed. Thus, the inventors are the first to determine a role for Sp100 in oncogenesis, cell senescence, and reprogramming to pluripotency, specifically in regulating the balance between cell senescence, stem cell-like replication and malignant transformation.

I. CELL COMPOSITIONS COMPETENT FOR REPROGRAMMING

Thus, in one aspect, a composition of somatic cells or a composition of isolated somatic cells that are competent for reprogramming is provided. By "competent for reprogramming" is meant that the cells described herein have the capacity to spontaneously alter their global transcriptome in cell culture, e.g., on a practical laboratory scale of 1, 2, 3, 4, 5 or more cell culture vessels, to obtain cells with markers of pluripotency, such as but not limited to POU5F1 (OCT4), TERT, SOX2, NANOG, and CDH1 (E-Cadherin), without the exogenous administration of TERT, SOX2, POU5F1 (OCT4), NANOG, LIN28, MYC, or KLF4. As such, the somatic cells that are competent for reprogramming described herein are unlike any other reported normal cultured human cell type or composition previously described that involve the introduction of genes, RNA, or protein factors such as TERT, SOX2, POU5F1 (OCT4), NANOG, LIN28, MYC, or KLF4, or that involve reprogramming to pluripotency by nuclear transfer or the contact of said somatic cell with protein components of oocytes or undifferentiated cells. Furthermore, the compositions described herein that comprise somatic cells made competent for reprogramming by down-regulating the level or activity of Sp100 differ significantly from normal embryonic stem cells or induced pluripotent stem cells. For example, embryonic stem cells or induced pluripotent stem cells form benign teratomas when transplanted in vivo, while the compositions described herein which comprise somatic cells made competent for reprogramming are a heterogeneous culture of cells capable of forming malignant tumors when transplanted in vivo. Additionally, the compositions described herein comprising somatic cells made competent for reprogramming by down-regulating the level or activity of Sp100 may be used to generate purified cultures of cells expressing pluripotency markers through cultivation in conditions conducive to the growth of embryonic stem cells or induced pluripotent stem cells. Such conditions include, for example, cultivation in FGF2-containing medium with or without feeder cells (see, e.g., U.S. Pat. No. 7,439,064, incorporated by reference herein). Other cultivation conditions that may be suitable for use are described in the art; see, e.g., U.S. Pat. Nos. 7,892,830; 7,514,260; 7,449,334; 7,029,913; 6,200,806 and 5,843,780, incorporated by reference herein. The compositions described herein comprising somatic cells made competent for reprogramming by down-regulating the level or activity of Sp100, after such cultivation, are then differentiated (in vitro or in vivo) into cells and tissues of different types of lineages than the original somatic cell.

As still another embodiment, the cell compositions described herein have characteristics of an increased lifespan relative to original or parent cells. The increased lifespan is demonstrated herein by the increased passage number (cell divisions) achieved by the reprogrammed cells (e.g., the BJsm cells described in the examples below), and reduction of senescence. Desirably, the cell compositions provided herein or nuclei obtained therefrom can be differentiated into a cell of a different cell type or lineage.

This capacity can be developed by propagating the cell compositions described herein with nutrient media, including the clonal propagation of derivative cell types (see e.g., US patent application publication No. 2010/0184033, incorporated herein by reference), and under conditions known to permit the development and differentiation of stem cells into desired cells types. Such desired cell types include, e.g., cells that exhibit different morphological, physiological, functional, and/or immunological features than exhibited by the original cells. Thus, a composition described herein can also include a differentiated cell composition characterized by expression of genetic markers of various cell lineages, including without limitation, markers for skeletal and cardiac muscle, neural, adipocyte, osteoclast, osteoblast, vascular endothelial, perivascular cells, hematopoietic, astrocytes, renal, retinal, cornea, and hepatocyte lineages.

As used herein, the term "somatic cell" or "somatic parent cell" includes any mammalian cell that has lost pluripotency as a result of differentiation, has entered a germ layer lineage such as endodermal, mesodermal, ectodermal, and neural crest-derived cells, and that normally expresses detectable levels of Sp100 protein. In another embodiment, the somatic cells are human cells. In another embodiment, the somatic cells are obtained from a veterinary or farm animal, a domestic animal or pet, or animal, particularly a primate, normally used for clinical research. In certain embodiments, the selected somatic parent cell can be an autologous cell obtained from a subject in need of a therapeutic treatment. Such a somatic parent cell can be manipulated according to the methods described herein to reduce or eliminate its normal Sp100 levels, and permit it to be propagated. In another embodiment, the selected parent somatic cell may be obtained from a different donor, e.g., in circumstances in which the subject to be treated has a condition in which his own somatic cells may carry disease or genetic disorder, or where autologous donation is not suitable. Such a somatic cell can be manipulated according to the methods described herein to reduce or eliminate its normal Sp100 levels, and permit it to be propagated, and can be further manipulated or genetically matched to avoid rejection by the subject's immune system. In one aspect, the parent somatic cells are human fibroblast cells. In another embodiment, the parent somatic cells are human fibroblast cells derived from human foreskin.

In one embodiment, this composition of somatic cells is characterized by a reduction in the normal level of Sp100 that is present in the parent somatic cell. In another embodiment, the cells of the composition are characterized by a reduction in the normal levels of all Sp100 isoforms. In another embodiment, the cells of the composition are characterized by an elimination of the normal levels of one or more Sp100 isoforms.

In another embodiment, a composition of somatic cells is provided which are competent for reprogramming and are characterized by a reduction or elimination of Sp100 expression and by the presence of at least one genetic marker of pluripotent stem cells. In one embodiment, the somatic cells having reduced or eliminated Sp100 expression carry the gene expression marker TERT. In one embodiment, the somatic cells having reduced or eliminated Sp100 expression carry the marker, LIN28B. In one embodiment, the somatic cells having reduced or eliminated Sp100 expression carry the gene expression marker SOX2. In one embodiment, the somatic cells having reduced or eliminated Sp100 expression carry the gene expression marker, NANOG. In one embodiment, the somatic cells having reduced or eliminated Sp100 expression carry the gene expression marker POU5F1 (OCT4). In still other embodiments, the cells carry two of more of the gene expression markers TERT, LIN28B, SOX2, NANOG and OCT4 or their protein counterpart markers. In one embodiment, a composition of somatic cells having reduced or eliminated Sp100 expression also express the cells markers of pluripotency including TERT, LIN28B, SOX2, NANOG and OCT4.

In another embodiment, these somatic cells that are competent for reprogramming carry genetic markers that can include one or more of the additional markers identified in Table 2's list of genes and FIG. 4A, 4B or 4C. In another embodiment, the Sp100-reduced or eliminated cells are characterized by a change from the normal cell's pattern of expression of two or more of the genetic markers identified in Table 2 and FIG. 4A, 4B or 4C. In still other embodiment, the cells are characterized by a change in the pattern of expression of at least 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 of the genetic markers identified in Table 2 and FIG. 4A, 4B or 4C.

TABLE 2

Forward (F) and Reverse (R) primers used for semi-quantitative and quantitative RT = PCR

| GENE | PRIMER SEQUENCES | Seq ID No. | T | SIZE (bp) |
|---|---|---|---|---|
| LIN28B | F: CCTCCTCAGCCAAAGAAGTG | 1 | 60 | 181 |
|  | R: GTGGTGATGTACAGCCATGC | 2 |  |  |
| FGF2 | F: CTTCTCTGTACCCATACAGC | 3 | 58 | 530 |
|  | R: CAGGTAGATAAGCCTCCAAG | 4 |  |  |
| POU5F1 | F: TGGTCCGAGTGTGGTTCTGTAA | 5 | 60 | 64 |
|  | R: TGTGCATAGTCGCTGCTTGAT | 6 |  |  |
| MGMT | F: GCCGGCTCTTCACCATCCCG | 7 | 60 | 211 |
|  | R: GCTGCAGACCACTCTGTGGCACG | 8 |  |  |
| PML4 | F: GCAGCTCGGAAGACTC | 9 | 60 | 203 |
|  | R: GTAGCCCCAGGAGAAC | 10 |  |  |
| DAXX | F: CGGCGGCTGCAGGAAAAGGAGT | 11 | 60 | 474 |
|  | R: GCGCCGGGCCAACACAGGA | 12 |  |  |
| MYC | F: CGTCTCCACACATCAGCACAA | 13 | 58 | 66 |
|  | R: TTGGCAGCAGGATAGTCCTT | 14 |  |  |
| KLF4 | F: GTTTTGAGGAAGTGCTGAG | 15 | 55 | 332 |
|  | R: CAGTCACAGTGGTAAGGTTT | 16 |  |  |
| SOX2 | F: GGGAAATGGGAGGGGTGCAAAAGAGG | 17 | 60 | 125 |
|  | R: TTGCGTGAGTGTGGATGGGATTGGTG | 18 |  |  |
| Sp100A | F: TGGGAACTCCTTTTTGCATT | 19 | 60 | 231 |
|  | R: CAAACGACAATGATGTCAACC | 20 |  |  |
| Sp100B | F: AGGAGCGATTCAAACAAGGA | 21 | 60 | 236 |
|  | R: AGACGAGACATTGGCAGAAG | 22 |  |  |
| Sp100C | F: AAGCCAATCAGGTCATCAGG | 23 | 60 | 243 |
|  | R: ATGTCCTGCACAAACCCTTC | 24 |  |  |
| Sp100HMG | F: TAGCCCTGTCCTGGTGGTAT | 25 | 60 | 247 |
|  | R: TGTCAACAAAACAGCTGCAA | 26 |  |  |
| TERT | F: CGGAAGAGTGTCTGGAGCAA | 27 | 58 | 145 |
|  | R: GGATGAAGCGGAGTCTGGA | 28 |  |  |
| HSPA1A | F: CAGGTGATCAACGACGGAGACA | 29 | 60 | 363 |
|  | R: GTCGATCGTCAGGATGGACACG | 30 |  |  |
| NANOG | F: CAAAGGCAAACAACCCACTT | 31 | 60 | 158 |
|  | R: TCTGCTGGAGGCTGAGGTAT | 32 |  |  |
| KRAS | F: AGGCCTGCTGAAAATGACTG | 33 | 60 | 256 |
|  | R: TACACAAAGAAAGCCCTCCC | 34 |  |  |
| BMP7 | F: ACGCTTCGACAATGAGACGTTC | 35 | 60 | 572 |
|  | R: TGGCGTTCATGTAGGAGTTCAG | 36 |  |  |
| CDH1 | F: GAACGCATTGCCACATACACT | 37 | 60 | 745 |
|  | R: CTGTGGAGGTGGTGAGAGAGA | 38 |  |  |
| ACTA2 | F: AGGAAGGACCTCTATGCTAACAAT | 39 | 59 | 355 |
|  | R: AACACATAGGTAACGAGTCAGAGC | 40 |  |  |
| GAPDH | F: CTGGGCTACACTGAGCACCAG | 41 | 60 | 74 |
|  | R: CCAGCGTCAAAGGTGGAG | 42 |  |  |

As demonstrated by the examples below, normal somatic cells that express Sp100 or one of its isoforms, may be "reprogrammed" by modulating the normal activity of Sp100 in the cells. Such modulation allows one to reversably regulate replicative senescence in a somatic cell and competence for reprogramming and malignant transformation by modulating the expression of Sp100 therein. In one embodiment, the expression of Sp100 is reduced or eliminated in the cell, thereby retarding senescence of the cell, and permitting the cell to be serially propagated to express the pluripotency markers discussed above. In another embodiment, the expression of Sp100 is increased or reintroduced in the cell, thereby returning the cell to a replication limited and differentiation-committed stage.

Such modulation of the expression of the Sp100 isoforms identified above may be achieved using now-conventional genetic engineering methods that may be selected by one of skill in the art. In one embodiment, the selected cells are transfected with plasmids or virus vectors that express nucleic acid sequences that can either reduce or silence expression of the desired Sp100 protein in a transient or stable manner. In another embodiment, the cells are transfected with plasmids or virus vectors that express nucleic acid sequences that encode for expression of the desired Sp100 protein in a transient or stable manner where an increase in Sp100 protein expression is desired. Such plasmid or vector constructs can be desirably manipulated to contain inducible promoters, suicide genes, and the like to enable the silencing of the Sp100 expression or induction of Sp100 expression as desired. Any method of increasing or decreasing expression of Sp100 in a selected cell is anticipated to be useful in this invention and selection of such methods and the components thereof are not limited to the methods described herein below or in the examples.

Generating the cell compositions described herein to down-regulate or extinguish or modulate Sp100 expression in cells may employ methods and components as described herein. Such methods can employ a variety of components known to one of skill in the art and be achieved in multiple ways.

A short nucleic acid molecule useful in the compositions and in the methods described herein is any nucleic acid molecule capable of inhibiting or down-regulating Sp100 gene expression. Typically, short interfering nucleic acid molecules are composed primarily of RNA, and include siRNA or shRNA, as defined below. A short nucleic acid molecule may, however, include nucleotides other than RNA, such as in DNAi (interfering DNA), or other modified bases. Thus, the term "RNA" as used herein means a molecule comprising at least one ribonucleotide residue and includes double stranded RNA, single stranded RNA, isolated RNA, partially purified, pure or synthetic RNA, recombinantly produced RNA, as well as altered RNA such as analogs or analogs of naturally occurring RNA. In one embodiment the short nucleic acid molecules of the present invention is also a short interfering nucleic acid (siNA), a short interfering RNA (siRNA), a double stranded RNA (dsRNA), a micro RNA, and/or a short hairpin RNA (shRNA) molecule. The short nucleic acid molecules can be unmodified or modified chemically. Nucleotides of the present invention can be chemically synthesized, expressed from a vector, or enzymatically synthesized.

In some embodiments, the short nucleic acid comprises between 18 and 60 nucleotides. In another embodiment, the short nucleic acid molecule is a sequence of nucleotides between 25 and 50 nucleotides in length. In still other embodiments, the short nucleic acid molecule ranges up to 35 nucleotides, up to 45, up to 55 nucleotides in length, depending upon its structure. These sequences are designed for better stability and efficacy in knockdown (i.e., reduction) of Sp100 gene expression. In one embodiment, the nucleic acid molecules described herein comprises sufficient nucleotides complementary to a Sp100 nucleic acid sense sequence, particularly an open reading frame of Sp100. In one embodiment, the nucleic acid molecules described herein comprises at least 20, 25, 30, 35, 40, 45, 50, 55 or 60 or more nucleotides complementary to a Sp100 antisense nucleic acid sequence strand. In one embodiment, the nucleic acid molecules described herein comprises 19-60 nucleotides complementary to a Sp100 nucleic acid sense sequence and comprises 19-60 nucleotides complementary to a Sp100 antisense nucleic acid sequence strand.

In one embodiment, a useful therapeutic agent is a small interfering RNA (siRNA) or a siRNA nanoparticle. siRNAs are double stranded, typically 21-23 nucleotide small synthetic RNA that mediate sequence-specific gene silencing, i.e., RNA interference (RNAi) without evoking a damaging interferon response. siRNA molecules typically have a duplex region that is between 18 and 30 base pairs in length. Sp100 siRNAs are designed to be homologous to the coding regions of Sp100 mRNA (e.g., see sequences in Table 1) and suppress gene expression by mRNA degradation. The siRNA associates with a multiprotein complex called the RNA-induced silencing complex (RISC), during which the "passenger" sense strand is enzymatically cleaved. The antisense "guide" strand contained in the activated RISC then guides the RISC to the corresponding mRNA because of sequence homology and the same nuclease cuts the target mRNA, resulting in specific gene silencing. The design of si/shRNA preferably avoids seed matches in the 3'UTR of cellular genes to ensure proper strand selection by RISC by engineering the termini with distinct thermodynamic stabilities. A single siRNA molecule gets reused for the cleavage of many target mRNA molecules. RNAi activity can be induced by the introduction of synthetic siRNAs.

In one embodiment, a siRNA molecule of the invention comprises a double stranded RNA wherein one strand of the RNA is complimentary to the RNA of Sp100. In another embodiment, a siRNA molecule of the invention comprises a double stranded RNA wherein one strand of the RNA comprises a portion of a sequence of RNA having Sp100 sequence. SiRNAs for Sp100 may be purchased commercially or designed by resort to conventional methods.

In one embodiment, siRNA without any chemical modification having high stability and specificity for Sp100, are useful in generating the reprogrammed competent cells or may be used in combination with other reprogramming agents identified in the documents cited herein. In another embodiment, siRNA oligonucleotides targeting Sp100 are complexed or conjugated to a polymer or any other material that stabilizes siRNA.

Among such stabilizing polymers and materials are polyethyleneimine (PEI), which may be conjugated to siRNA, resulting in the generation of nanocomplexes of about 50 nm, as described in Cubillos-Ruiz J R, et al, 2009 J. Clin. Invest., 119(8):2231-44, incorporated by reference herein. In another embodiment, such a stabilizing material is chitosan. In one embodiment, the siRNA is in a stable composition, with or without conjugation, with cholesterol. In still other embodiments, siRNA may be combined with conjugates such as a lipid, a cationic lipid, a phospholipid, and a liposome.

In another embodiment, the siRNA is in a stable composition, with or without conjugation, to an antibody or fragment thereof that permits the siRNA to be preferentially targeted. In one embodiment, the antibody is an antibody or fragment to a desirable somatic cell receptor. In another embodiment, the antibody is an antibody or fragment to a T cell surface marker, a T cell receptor or a chimeric receptor which also permits targeting. For example, in one another embodiment, the siRNA are linked to thiolated F(ab)2 fragments of monoclonal antibodies targeting T cell surface markers (e.g., CD3, CTLA4, CD44, CD69 or CD25). In another embodiment, the antibody or fragment is to a T cell receptor or chimeric receptor. T cell receptors or chimeric receptors for association with, or co-expression with the siRNA include without limitation, TCRs against human antigens. Among such useful TCRs include those that have been transduced in adoptively transferred T cells (reviewed in Trends Biotechnol. 2011 November; 29(11):550-7). In one embodiment, the TCR is the receptor that binds human carcinoembryonic antigen (Parkhurst M R et al, 2011 Mol. Ther., 19(3):620-6), NY-ESO-1 (Robbins P F et al, 2011 J. Clin. Oncol., 29(7):917-24), MAGE-A3 (Chinnasamy N et al 2011 J. Immunol., 186(2):685-96) and MART-1, gp100 and p53 (Morgan R A et al, 2006 Science, 314(5796):126-9). Association with such TCRs is described in Westwood et al, 2005, cited herein.

In another embodiment, the short nucleic acid molecule is a small hairpin RNA (shRNA). An shRNA molecule useful in the methods and compositions described herein is generally defined as an oligonucleotide containing an about 18-23 nucleotide siRNA sequence followed by a ~9-15 nt loop and a reverse complement of the siRNA sequence. The loop nucleotides generally form a non-coding sequence. shRNA sequences targeting human Sp100 are commercially available, or known to the art (e.g., Santa Cruz Biotechnology, Inc., SantaCruz, Calif.; and GeneCopoeia, Rockville, Md.), along with their mature and antisense strands. shRNAs can be cloned in plasmids or in non-replicating recombinant viral vectors to endogenously/intracellularly express shRNA, which is subsequently processed in the cytoplasm to siRNA. The shRNA effects are longer lasting because they are continually produced within the cells and thus have an effect that lasts the duration of the cell's life.

As used herein, a vector may include any genetic element including, without limitation, naked DNA, a phage, transposon, cosmid, episome, plasmid, bacteria, or a virus. As used herein, the term vector refers to a genetic element which expresses, or causes to be expressed, the desired construct that modulates, inhibits or silences, the expression of Sp100 in the parent somatic cell ex vivo or in vivo. These shRNAs can be produced in plasmid based systems, of which many are commercially available. However, because they are easy to deliver, non-replicating recombinant viral vectors are commonly used for shRNA expression. Thus, in one embodiment, the vector is a non-pathogenic virus. In another embodiment, the vector is a non-replicating virus. In one embodiment, a desirable viral vector may be a retroviral vector, such as a lentiviral vector. In another embodiment, a desirable vector is an adenoviral vector. In still another embodiment, a suitable vector is an adeno-associated viral vector. Adeno, adeno-associated and lentiviruses are generally preferred because they infect actively dividing as well as resting and differentiated cells such as the stem cells, macrophages and neurons. A variety of adenovirus, lentivirus and AAV strains are available from the American Type Culture Collection, Manassas, Va., or available by request from a variety of commercial and institutional sources, including those listed herein. Further, the sequences of many such strains are available from a variety of databases including, e.g., PubMed and GenBank.

In one embodiment, a lentiviral vector is used. Among useful vectors are the equine infectious anemia virus and feline as well as bovine immunodeficiency virus, and HIV-based vectors. A variety of useful lentivirus vectors, as well as the methods and manipulations for generating such vectors for use in transducing cells and expressing heterologous genes are described in N Manjunath et al, 2009 Adv Drug Deliv Rev., 61(9): 732-745, incorporated herein by reference. In one embodiment the self-inactivating lentiviral vector (GeMCRIS 0607-793) which was successfully used to transduce T cells directed against tumor cells in leukemia patients (Porter et al., N Engl J Med. 2011 Aug. 25; 365(8):725-33) is useful to carry and express a nucleotide sequence, e.g., an shRNA, that inhibits the expression of Sp100. See the description of one such desirable vector in Negorev D G et al, 2009 J. Virol., 83:5168-80 and Everett R D et al, 2008 J. Virol., 82:2661-72.

In another embodiment, the vector used herein is an adenovirus vector. Such vectors can be constructed using adenovirus DNA of one or more of any of the known adenovirus serotypes. See, e.g., T. Shenk et al., *Adenoviridae: The Viruses and their Replication*", Ch. 67, in FIELD'S VIROLOGY, $6^{th}$ Ed., edited by B. N Fields et al, (Lippincott Raven Publishers, Philadelphia, 1996), p. 111-2112; U.S. Pat. No. 6,083,716, which describes the genome of two chimpanzee adenoviruses; U.S. Pat. No. 7,247,472; WO 2005/1071093, etc. One of skill in the art can readily construct a suitable adenovirus vector to carry and express a nucleotide sequence as described herein, e.g., a shRNA that inhibits the expression of Sp100, by resort to well-known publications and patents directed to such viral vectors. See, e.g., Arts, et al, 2003 Adenoviral vectors for expressing siRNAs for discovery and validation of gene function, Genome Research, 13:2325-32.

In another embodiment, the vector used herein is an adeno-associated virus (AAV) vector. Such vectors can be constructed using AAV DNA of one or more of the known AAV serotypes. See, e.g., U.S. Pat. No. 7,906,111 (Wilson); Gao et al, Novel Adeno-Associated Viruses From Rhesus Monkeys as Vectors for Human Gene Therapy, PNAS, vol. 99, No. 18, pp. 11854-11859, (Sep. 3, 2002); Rutledge et al, Infectious Clones and Vectors Derived from Adeno-Associated Virus (AAV) Serotypes Other Than AAV Type 2, Journal of Virology, vol. 72, pp. 309-319, (January 1998). One of skill in the art can readily construct a suitable AAV vector to carry and express a nucleotide sequence as described herein, e.g., an shRNA that inhibits the expression of Sp100, by resort to well-known publications and patents directed to such AAV vectors. See, e.g., Grimm et al, Adeno-associated virus vectors for short hairpin RNA expression, Methods Enzymology, 392, 381-405 (2005); U.S. Pat. No. 7,803,611; U.S. Pat. No. 7,696,179.

In yet another embodiment, the vector used herein is a bacterial vector. In one embodiment, the bacterial vector is *Listeria monocytogenes*. *Listeria monocytogenes* is a food borne pathogen which has been found to be useful as a vaccine vehicle, especially in attenuated form. See, e.g., Ikonomidis et al, J. Exp. Med, 180:2209-18 (December 1994); Lauer et al, Infect. Immunity, 76(8):3742-53 (August 2008). In one embodiment, the bacterial vector is live-attenuated or photochemically inactivated. The heterologous gene of interest, e.g., the shRNA the can inhibit Sp100, can be expressed recombinantly by the bacteria, e.g., via a plasmid introduced into the bacteria, or integrated into the bacterial genome, i.e., via homologous recombination.

Generally, each of these vectors also comprises a minigene. By "minigene" is meant the combination of a selected nucleotide sequence (e.g., a short nucleic acid sequence described herein or shRNA that inhibits or silences the expression of Sp100) and the operably linked regulatory elements necessary to drive translation, transcription and/or expression of the gene product in the host cell in vivo or in vitro. As used herein, "operably linked" sequences include both expression control sequences that are contiguous with the gene of interest and expression control sequences that act in trans or at a distance to control the gene of interest.

These vectors also include conventional control elements that permit transcription, translation and/or expression of the shRNA in a cell transfected with the plasmid vector or infected with the viral vector. A great number of expression control sequences, including promoters which are native, constitutive, inducible and/or tissue-specific, are known in the art and may be utilized. In one embodiment, the promoter is an RNA polymerase promoter. In another embodiment, the promoter is an RNA polymerase promoter selected from U6, H1, T7, pol I, pol II and pol III promoters. In another embodiment, the promoter is a constitutive promoter. In another embodiment, the promoter is an inducible promoter. In one embodiment, the promoter is selected based on the chosen vector. In another embodiment, when the vector is lentivirus, the promoter is U6, H1, CMV IE gene, EF-1α, ubiquitin C, or phosphoglycerokinase (PGK) promoter. In another embodiment, when the vector is an AAV, the promoter is an RSV, U6, or CMV promoter. In another embodiment, when the vector is an adenovirus, the promoter is RSV, U6, CMV, or H1 promoters. In another embodiment, when the vector is Listeria monocytogenes, the promoter is a hly or actA promoter. Still other conventional expression control sequences include selectable markers or reporter genes, which may include sequences encoding geneticin, hygromicin, ampicillin or purimycin resistance, among others. Other components of the vector may include an origin of replication. Selection of these and other promoters and vector elements are conventional and many such sequences are available (see, e.g., texts such as Sambrook et al, Molecular Cloning: A Laboratory Manual, Cold Spring Harbor Press, Cold Spring Harbor, N.Y., and references cited therein).

These vectors are generated using the techniques and sequences provided herein, in conjunction with techniques known to those of skill in the art. Such techniques include conventional cloning techniques of cDNA such as those described in texts (see, e.g., Sambrook et al, cited above), use of overlapping oligonucleotide sequences, polymerase chain reaction, and any suitable method which provides the desired nucleotide sequence.

Thus, in one embodiment, using the information taught herein and publically available and known vector construction components and techniques, one of skill in the art can construct a viral vector (or plasmid) that expresses the desired construct, e.g., a short hairpin (shRNA) sequence that suppresses the expression of Sp100. In still another embodiment, the vector may be designed to co-express more than one shRNA that suppresses the expression of Sp100 or more than one isoform of Sp100.

In yet another embodiment, the vector may be designed to co-express a construct that enables targeting of the virus vector to only certain somatic cells, e.g., if in vivo delivery of the viral vector is desired. Such targeting will enable the virus to be employed in vivo. For example, the virus vector is designed to co-express a specific cell receptor or a chimeric cell receptor, or portion of an antibody or fragment to a specific cell surface marker. Among suitable constructs for co-expression are fragments of monoclonal antibodies targeting cell surface markers (e.g., CD3, CTLA4, CD44, CD69 or CD25), TCRs against human antigens, such as human carcinoembryonic antigen, NY-ESO-1, MAGE-A3 and MART-1, gp100 and p53.

In still other embodiments, the viral vectors or plasmids carrying the Sp100 shRNA are complexed or conjugated to a polymer or any other material that stabilizes the vector or assists in its targeting. Among such stabilizing polymers and materials are polyethyleneimine (PEI), which may be conjugated to the vector, resulting in the generation of nanocomplexes of about 50 nm, as described in Cubillos-Ruiz J R, et al, 2009 J. Clin. Invest., 119(8):2231-44, incorporated by reference herein. In another embodiment, such a stabilizing material is chitosan. In one embodiment, the vector is in a stable composition, with or without conjugation, with cholesterol. In another embodiment, the vector may be conjugated, to an antibody or fragment thereof that permits the vector to be preferentially targeted. In one embodiment, the antibody is an antibody or fragment to a desirable molecule, such as a specific cell receptor. For example, in one another embodiment, the vectors are linked to thiolated F(ab)2 fragments of monoclonal antibodies targeting desired cell surface markers In some embodiments, the method of developing the cell compositions that have the replication characteristics and cell markers of differentiating stem cells further involves serially propagating the cells having reduced Sp100 levels to yield cells with markers of pluripotent stem cells, such as the markers identified above. In one embodiment, the cells of the invention are cultured for up to 9 passages. In another embodiment, the cells of the invention are cultured for at least 10 passages. In another embodiment, the cells are cultured for at least 11 passages. In another embodiment, the cells are cultured for at least 12 passages. In another embodiment, the cells are cultured for at least 13 passages. In another embodiment, the cells are cultured for at least 14, 15, 16, 17, 18, 19, 20, 21, 22, 23, 24, 25 or 30 or more passages.

The cells expressing the desired cell markers may be isolated from culture and there after propagated in a variety of selected media which supply to the Sp100-reduced cells other components necessary to permit the cells to differentiate. See, e.g., the media described in the following examples or in the publications referenced herein. For example, once the Sp100 expression is reduced or silenced, the cells are propagated and cells that express markers of pluripotent stem cells and demonstrate unrestricted cell division are identified and isolated. In one embodiment, this method is performed ex vivo. In another embodiment, the method produces cells characterized by increased telomerase activity or telomerase length.

In still other aspects, the cell compositions characterized by reduced or extinguished Sp100 expression and that carry the cell markers described above may be further manipulated to permit the cells to differentiate into a specific type of cell or tissue by subjecting the cells to further treatment, such as the treatments described in detail in the US Patent Publications Nos. 2011/0286978, 2011/0171185 and 2010/0184033, incorporated by reference herein.

The cell compositions comprising the small nucleic acid molecules, viruses, or plasmids described above may be further associated with a pharmaceutically acceptable carrier. As used herein the term "pharmaceutically acceptable carrier" or "diluent" is intended to include any and all solvents, dispersion media, coatings, antibacterial and antifungal agents, isotonic and absorption delaying agents, and the like, compatible with administration to human cells ex vivo or to humans directly. In one embodiment, the diluent is saline or buffered saline.

These cell compositions can be manipulated for use in a variety of research, diagnostic and therapeutic indications. For example, cells differentiated from such cell compositions may be used in transplantation or grafting, and ultimately for the replacement of body tissues, organs, components or structures damaged due to disease, trauma, or age, among other causes. See, e.g., the published US patent applications cited above.

II. SP100 AS A SUPPRESSOR OF UNRESTRICTED CELL REPLICATION

The term "neoplastic disease", "cancer" or "proliferative disease" as used herein refers to any disease, condition, trait, genotype or phenotype characterized by unregulated or abnormal cell growth, proliferation or replication. The abnormal proliferation of cells may result in a localized lump or tumor, be present in the lymphatic system, or may be systemic. In one embodiment, the neoplastic disease is benign. In another embodiment, the neoplastic disease is pre-malignant, i.e., potentially malignant neoplastic disease. In a further embodiment, the neoplastic disease is malignant, i.e., cancer. In still a further embodiment the neoplastic disease may be caused by viral infection.

In one embodiment, the neoplastic disease is an epithelial cancer. In various embodiments of the methods and compositions described herein, the cancer can include, without limitation, breast cancer, lung cancer, prostate cancer, colorectal cancer, brain cancer, esophageal cancer, stomach cancer, bladder cancer, pancreatic cancer, cervical cancer, head and neck cancer, ovarian cancer, melanoma, leukemia, myeloma, lymphoma, glioma, and multidrug resistant cancer. In another embodiment, the neoplastic disease is Kaposi's sarcoma, Merkel cell carcinoma, hepatocellular carcinoma (liver cancer), cervical cancer, anal cancer, penile cancer, vulvar cancer, vaginal cancer, neck cancer, head cancer, multicentric Castleman's disease, primary effusion lymphoma, tropical spastic paraparesis, adult T-cell leukemia, Burkitt's lymphoma, Hodgkin's lymphoma, post-transplantation lymphoproliferative disease, nasopharyngeal carcinoma, pleural mesothelioma cancer of the lining of the lung), osteosarcoma (a bone cancer), ependymoma and choroid plexus tumors of the brain, and non-Hodgkin's lymphoma. In still other embodiments, the cancer may be a systemic cancer, such as a leukemia.

The term "benign" condition as used herein refers to a condition which is not a neoplastic disease, i.e., the benign condition is not cancer. In one embodiment, the benign condition is a wart, such as common warts, plantar warts, subungal warts, or periungual warts, or flat warts, genital or anal warts. In yet a further embodiment, the benign condition is respiratory papillomatosisor epidermodysplasia verruciformis. Still other benign conditions caused by uncontrolled cell proliferation are included herein.

In one aspect, a method for retarding the growth of or suppressing unwanted cell proliferation comprises expressing, inducing expression of, upregulating or increasing, Sp100 in a targeted cell that is undergoing unrestricted proliferation or replication. As discussed further in this specification, the terms "expressing," "inducing expression of", "upregulating" or "increasing" are meant to include upregulating or increasing the expression of Sp100 at the nucleic acid level, and/or increasing the protein expression levels of the Sp100 protein. Methods of increasing either mRNA expression and protein expression levels of Sp100 in the targeted cell are within the skill of the art given the disclosure herein.

In one embodiment, the targeted cell is a benign or premalignant cell. In one embodiment, the targeted cell is a cancer cell, as described above. In another embodiment, the targeted cell is a tumor cell, as described above. In another aspect, the method is designed to increase exposure to Sp100 in the environment or microenvironment of the targeted cell. The targeted cell undergoing unrestricted growth or replication either does not express Sp100 or expresses insufficient Sp100 to suppress uncontrolled growth of the cells.

In one embodiment, this method comprises delivering to a targeted cell undergoing unrestricted or abnormal proliferation or replication a vector which expresses a nucleotide sequence encoding Sp100 under the control of a selected expression system. The Sp100 is selected from the group consisting of an isoform of Sp100, a naturally occurring variant of Sp100, a modified Sp100 molecule or fragment of Sp100 that retains the growth suppressing activity of the native molecule. Such methods can be accomplished ex vivo, such as by delivering viral vectors or plasmids that express Sp100 to a targeted cell or to an anti-tumor T cell for autologous transfer. In another embodiment, the method involves direct delivery of the Sp100-expressing compositions to the subject.

Thus, in one embodiment, a method of treating a proliferative disease, e.g., cancer, or enhancing an anti-tumor response in a subject having a cancer involves administering to a subject in need thereof a therapeutic reagent that up-regulates, induces, or provides for the expression of Sp100 in T cells within the environment of the targeted cells, e.g., cancer cells. In one embodiment, the proliferative disease is characterized by the presence of a solid tumor and Sp100 is desirably expressed in the tumor cells or T cells within the tumor microenvironment. These methods are particularly useful for enhancing the treatment of cancer, particularly cancers that are not sensitive to other conventional treatments.

In one embodiment, the method involves administering a nucleic acid molecule, such as a plasmid or viral vector in a suitable pharmaceutically acceptable carrier to the subject. In another embodiment, the nucleic acid molecule, plasmid or vector is carried via adoptive transfer within a targeted cell, cancer cell or anti-tumor T cell for autologous transfer. In still another embodiment, the targeted cell or anti-tumor T cell may be provided by an HLA-matched donor.

The generation of a suitable plasmid vector that transiently or stably expresses an isoform of Sp100 is within the skill of the art, and employs many of the techniques described above and in texts such as Sambrook et al, cited above, but modified to generate expression of Sp100, rather than it's silencing. Thus in place of an shRNA sequence or si nucleic acid sequence, the vectors deliver a sequence that encodes an isoform of Sp100, such as those identified in Table 1 above. However, similar vector constructs such as the minigenes, and including more extensive promoters, and vector elements can be used in a similar manner, as is known in the art.

In one embodiment, the method provides administering a vector which encodes a construct that expresses Sp100, in a pharmaceutically acceptable carrier or diluent. In one embodiment, a viral vector expressing Sp100 can be employed to infect targeted cells, e.g., tumor cells or anti-tumor T cells in the tumor environment, and Sp100 is expressed or upregulated in the infected/transfected targeted cells or T cells. In another embodiment, a plasmid or viral vector expresses the Sp100-encoding sequence under the control of regulatory sequences. In one embodiment, the viral vector is selected from the group consisting of adenovirus, AAV or lentivirus. In another embodiment, the viral vector is complexed with a polymer. In one embodiment, the polymer is PEI, chitosan or any other material that stabilizes the virus. In another embodiment, the method provides administering a viral vector that co-expresses an anti-tumor T cell receptor or a chimeric anti-tumor T cell receptor. Anti-tumor T cells in the tumor environment become infected by the virus in vivo and Sp100 is expressed in the infected T cells.

In another embodiment, the method involves adoptive T cell therapy and involves administering an anti-tumor T cell or targeted cell transduced or transfected ex vivo with the viral vector, wherein the expression of Sp100 in the T cell or targeted cell, e.g., tumor cell, is upregulated or produced de novo in the cells. To generate cells for adoptive transfer, a plasmid or viral vector carrying a minigene expressing Sp100, and optionally a second construct for co-expression, are delivered to a sample of the subject's targeted cells, e.g., tumor cell, or to an anti-tumor T cell. "Anti-tumor T cells" are primarily, but not exclusively, CD8 (cytotoxic) T cells with activity against an autologous tumor, which are able to become activated and expand in response to antigen. Anti-tumor T cells, useful for adoptive T cell transfer include, in one embodiment, peripheral blood derived T cells genetically modified with receptors that recognize and respond to tumor antigens. Such receptors are generally composed of extracellular domains comprising a single-chain antibody (scFv) specific for tumor antigen, linked to intracellular T cell signaling motifs (see, e.g., Westwood, J. A. et al, 2005, Proc. Natl. Acad. Sci., USA, 102(52):19051-19056). Other anti-tumor T cells include T cells obtained from resected tumors. In another embodiment, the T cell is a polyclonal or monoclonal tumor-reactive T cell, i.e., obtained by aphaeresis, expanded ex vivo against tumor antigens presented by autologous or artificial antigen-presenting cells. In another embodiment, the T cell is engineered to express a T cell receptor of human or murine origin that recognizes a tumor antigen.

In one embodiment, T cells are designed for autologous adoptive transfer into patients having a proliferative or neoplastic disease, e.g., cancer. The T cells are engineered ex vivo to express a nucleic acid sequence encoding Sp100 once the T cells are delivered to the subject. In another embodiment, the subject's T cells can be manipulated in vivo by administration of a virus engineered to express the Sp100 coding sequence. Generally, when delivering the vector comprising the minigene by transfection to the T cells or targeted cells, the vector is delivered in an amount from about 5 μg to about 100 μg DNA to about $1\times10^4$ cells to about $1\times10^{13}$ cells. In another embodiment, the vector is delivered in an amount from about 10 to about 50 μg DNA to $1\times10^4$ cells to about $1\times10^{13}$ cells. In another embodiment, the vector is delivered in an amount from about 5 μg to about 100 μg DNA to about $10^5$ cells. However, the relative amounts of vector DNA to the T cells or targeted cells may be adjusted, taking into consideration such factors as the selected vector, the delivery method and the host cells selected. The vector may be introduced into the T cells by any means known in the art or as disclosed above, including transfection, transformation and infection. The heterologous gene of interest, e.g., the Sp100, may be stably integrated into the genome of the host cell, stably expressed as episomes, or expressed transiently.

In still another embodiment, the T cells or targeted cells are primed/pulsed with and against a selected antigen characteristic of the cell undergoing unrestricted proliferation, e.g., the targeted cell. In one embodiment, such an antigen is a tumor-specific, antigen. In another embodiment, the T cells or targeted cells are primed/pulsed with and against multiple targeted cell antigens, e.g., tumor antigens, before transfection with the vector carrying the Sp100 sequence. In another example, polyclonal T cells primed against multiple tumor antigens are transduced with the above-described lentiviral vector encoding Sp100. These adoptive T cells are prepared by pulsing T cells with a selected cancer, or tumor-specific, antigen; transducing the pulsed T cells with a vector expressing a construct that expresses Sp100, and formulating said pulsed, transfected T cells with a suitable pharmaceutical carrier.

Alternatively, the T cells or targeted cells can be transfected ex vivo with multiple different viral vectors that express different Sp100 isoforms and/or express TCRs and/or chimeric receptors and using the same techniques as described above.

In one embodiment, the viral vector/plasmid is transduced ex vivo into a T cell or targeted cell, e.g., a tumor cell, and said T cell or targeted cell is introduced into the subject in the environment or location of the neoplastic (benign or malignant) cell in the patient's body. In one embodiment, the construct is administered ex vivo to a T cell selected from the group consisting of (a) a polyclonal/monoclonal tumor-reactive T cell, (b) a tumor-infiltrating lymphocyte generated from aphaeresis samples or isolated from a tumor of a cancer patient, and (c) a T cell conditioned for adoptive transfer. In one embodiment, the T cell or targeted cell is pulsed with tumor antigen prior to transduction with the viral vector/plasmid. In another embodiment, the T cell has been conditioned for adoptive transfer by pulsing ex vivo with a tumor-specific antigen before it is transduced with the virus vector. In still another embodiment, the virus stably expresses the construct in the T cell.

In another aspect, a pharmaceutical composition is provided that expresses, induces expression of, or upregulates, the level or activity of Sp100 in cells of a subject in need thereof. In one embodiment, the composition comprises a viral vector that expresses Sp100 under the control of suitable regulatory sequences and a pharmaceutically acceptable carrier. In another embodiment, the composition comprises an autologous targeted cell, e.g., a tumor cell, transfected ex vivo with a viral vector that expresses Sp100 under the control of suitable regulatory sequences and a pharmaceutically acceptable carrier. In still another embodiment, the composition comprises an anti-tumor T cell transfected ex vivo with a viral vector that expresses Sp100 under the control of suitable regulatory sequences and a pharmaceutically acceptable carrier.

Expressing or up-regulating Sp100 levels or activity in targeted cells deficient in Sp100 or in anti-tumor T cells (conditioned for adoptive transfer or not) is theorized to enhance p53 tumor suppression, as indicated in the examples. Thus this therapeutic method increases the therapeutic activity of the T cells, and/or increases or activates tumor suppression in the tumor cells, and prolongs the survival of cancer patients. The therapeutic compositions administered by these methods, e.g., whether virus, virus nanoparticle, plasmid, or targeted cell or anti-tumor T cell treated for adoptive therapy, are administered directly into the environment of the targeted cell undergoing unwanted proliferation, e.g., a cancer cell or targeted cell (tumor) microenvironment of the patient. Conventional and pharmaceutically acceptable routes of administration include, but are not limited to, systemic routes, such as intraperitoneal, intravenous, intranasal, intravenous, intramuscular, intratracheal, subcutaneous, and other parenteral routes of administration or intratumoral or intranodal administration. Routes of administration may be combined, if desired. In some embodiments, the administration is repeated periodically.

These therapeutic compositions may be administered to a patient, preferably suspended in a biologically compatible solution or pharmaceutically acceptable delivery vehicle. The various components of the compositions are prepared for administration by being suspended or dissolved in a pharmaceutically or physiologically acceptable carrier such as isotonic saline; isotonic salts solution or other formulations that will be apparent to those skilled in such administration. The appropriate carrier will be evident to those skilled in the art and will depend in large part upon the route of administration. Other aqueous and non-aqueous isotonic sterile injection solutions and aqueous and non-aqueous sterile suspensions known to be pharmaceutically acceptable carriers and well known to those of skill in the art may be employed for this purpose.

The viral vectors or plasmids encoding Sp100 are administered in sufficient amounts to transduce the targeted cells or T cells and to provide sufficient levels of gene transfer and expression to produce or increase expression of Sp100 and provide a therapeutic benefit without undue adverse or with medically acceptable physiological effects, which can be determined by those skilled in the medical arts. In another embodiment, adoptive T cells are similarly administered to express the Sp100 to provide a therapeutic benefit without undue adverse or with medically acceptable physiological effects, which can be determined by those skilled in the medical arts.

Dosages of these therapeutic reagents will depend primarily on factors such as the condition being treated, the age, weight and health of the patient, and may thus vary among patients. For example, a therapeutically effective adult human or veterinary dosage of the viral vector is generally in the range of from about 100 µL to about 100 mL of a carrier containing concentrations of from about $1\times10^6$ to about $1\times10^{15}$ particles, about $1\times10^{11}$ to $1\times10^{13}$ particles, or about $1\times10^9$ to $1\times10^{12}$ particles virus. Methods for determining the timing of frequency (boosters) of administration will include an assessment of tumor response to the vector administration. As another example, the number of adoptively transferred targeted cells, e.g., tumor cells, or anti-tumor T cells can be optimized by one of skill in the art depending upon the response and overall physical health and characteristics of the individual patient. In one embodiment, such a dosage can range from about $10^5$ to about $10^{11}$ cells per kilogram of body weight of the subject. In another embodiment, the dosage of adoptively transferred targeted cells or anti-tumor T cells is about $1.5\times10^5$ cells per kilogram of body weight. In another embodiment, the dosage of adoptively transferred targeted cells or anti-tumor T cells is about $1.5\times10^6$ cells per kilogram of body weight. In another embodiment, the dosage of adoptively transferred targeted cells or anti-tumor T cells is about $1.5\times10^7$ cells per kilogram of body weight. In another embodiment, the dosage of adoptively transferred targeted cells or anti-tumor T cells is about $1.5\times10^8$ cells per kilogram of body weight. In another embodiment, the dosage of adoptively transferred targeted cells or anti-tumor T cells is about $1.5\times10^9$ cells per kilogram of body weight. In another embodiment, the dosage of adoptively transferred targeted cells or anti-tumor T cells is about $1.5\times10^{10}$ cells per kilogram of body weight. In another embodiment, the dosage of adoptively transferred targeted cells or anti-tumor T cells is about $1.5\times10^{11}$ cells per kilogram of body weight. Other dosages within these specified amounts are also encompassed by these methods. See, e.g., Dudley et al, 2002, cited above; and Porter et al, 2011, cited above.

In still other embodiments, these methods of expressing, inducing or up-regulating Sp100 are part of a combination therapy. In one embodiment, the nucleic acid molecules, such as the viral vectors, and the ex vivo-treated targeted cells, e.g., tumor cells, or anti-tumor T cells prepared for adoptive immunotherapy as described above, can be administered alone or in combination with various other treatments or therapies for the proliferative disease, e.g., cancer. In one embodiment, the method further comprises administering to the subject along with the therapeutic agent that expresses Sp100, an adjunctive therapy which may include a monoclonal antibody, chemotherapy, radiation therapy, a cytokine, or a combination thereof. These therapies may include co-expression of T cell receptor proteins or chimeric T cell receptor proteins in the same virus/plasmids/T cells as described above or administered to the subject in separate viruses/plasmids/T-cells.

In still another embodiment the methods herein may include co-administration or a course of therapy also using other small nucleic acid molecules or small chemical molecules or with treatments or therapeutic agents for the management and treatment of the proliferative disease, e.g., cancer. In one embodiment, a method of treatment of the invention comprises the use of one or more drug therapies under conditions suitable for said treatment.

In another embodiment of combination therapy, a passive therapeutic is administered that can immediately start eliminating the targeted cell undergoing unrestricted or abnormal replication or proliferation, e.g., tumor. This is accompanied by administration of active immunotherapy to induce an active endogenous response to continue the tumor eradication. In one embodiment, the methods described herein include administration of the Sp100-expressing or up-regulating therapeutic compositions described above with other known anti-proliferative disease therapies. For example, surgical debulking, in certain embodiments is a necessary procedure for the removal of large benign or malignant masses, and can be employed before, during or after application of the methods and compositions as described herein. Chemotherapy and radiation therapy, in other embodiments, bolster the effects of the methods described herein. Finally, immune-based therapies can eradicate residual disease and activate endogenous antitumor responses that persist in the memory compartment to prevent metastatic lesions and to control recurrences. Such combination approaches (surgery plus chemotherapy/radiation plus immunotherapy) are anticipated to be successful in the treatment of many proliferative diseases along with the methods described herein.

III. DRUG SCREENING AND DIAGNOSTIC USES OF SP100

In another aspect, a screen for a pharmaceutical composition capable of up-regulating or otherwise restoring the activity of Sp100 in abnormally proliferating/replicating cells, e.g., cancer cells, is provided. In one embodiment, cancer cell lines from e.g., lung, breast, colon, bladder, stomach, brain, pancreas, prostate, and other tissues are exposed to potential therapeutic molecules such as candidate small molecule drugs. Sp100 activity is measured or detected based on a reporter construct, such as the promoter element of SP100 driving a reporter gene (e.g., β-galactosidase) or a fluorescence gene (e.g., GFP), and used to identify agents capable of up-regulating Sp100 expression in the abnormally proliferating, e.g., cancer, cells.

In another aspect, a method for evaluating test agents or compounds for their pharmaceutical efficacy in up-regulating or otherwise restoring the Sp100 activity in cells characterizing a proliferative disease or disorder, e.g., cancer, is provided. In this method separate aliquots of cells characterizing a proliferative disease or disorder, e.g., tumor cells, are cultured in the presence and absence of the test compound. In one embodiment, the cells are derived from a cancer cell line selected from lung, breast, colon, bladder, stomach, brain, pancreas, and prostate. The level of Sp100 in each of the aliquots is then compared. In one embodiment, the Sp100 activity is measured based upon a reporter construct, such as the promoter element of Sp100 driving a reporter gene, inserted into the cells. In one embodiment, the reporter gene is beta galactosidase or a fluorescence gene, such as GFP. A significant increase in expression or activity of the reporter gene in the cells exposed to the test compound indicates the test compound has efficacy in up-regulating Sp100 cancer cells or other cells characterizing a proliferative disorder.

In another aspect, a method for evaluating test agents or compounds for their pharmaceutical efficacy in treating proliferative disease or disorder is provided. In this method separate aliquots of cells characterizing a proliferative disease or disorder, e.g., tumor cells, are cultured in the presence and absence of the test compound. In one embodiment, the cells are derived from a cancer cell line selected from lung, breast, colon, bladder, stomach, brain, pancreas, and prostate. The level of Sp100 in each of the aliquots is then compared. In one embodiment, the Sp100 activity is measured based upon a reporter construct, such as the promoter element of Sp100 driving a reporter gene, inserted into the cells. In one embodiment, the reporter gene is β-galactosidase or a fluorescence gene. A significant difference between the level of Sp100 in an aliquot maintained in the presence of (or exposed to) the test compound relative to the aliquot maintained in the absence of the test compound, indicates that the test compound has potential efficacy in treating the proliferative disease or disorder.

Test agents and compounds for screening and pharmaceutical use include but are not limited to peptides such as soluble peptides including Ig-tailed fusion peptides, members of random peptide libraries and combinatorial chemistry-derived molecular libraries made of D- and/or L-configuration amino acids, phosphopeptides (including members of random or partially degenerate, directed phosphopeptide libraries), antibodies [e.g. polyclonal, monoclonal, humanized, anti-idiotypic, chimeric, single chain antibodies, fragments, e.g. Fab, F(ab)$_2$, and Fab expression library fragments, and epitope-binding fragments thereof, polynucleotides (e.g. antisense, siRNA), and small organic or inorganic molecules. The agents or compounds may be endogenous physiological compounds or natural or synthetic compounds.

In yet another aspect, a method is provided for diagnosing a proliferative disease or disorder, e.g., cancer in a subject. The method includes measuring the level of expression or activity of a biomarker Sp100 in a biological sample from a mammalian subject, preferably a human subject. When compared to the level of expression or activity of Sp100 in a healthy mammalian subject, a decreased level of expression or activity is an indication of a diagnosis of proliferative disease or disorder.

In another aspect, a diagnostic method for proliferative disease or disorder involves measuring the level of expression or activity of Sp100 and at least one additional biomarker in the above-noted biological sample. The combined changes in expression or activity of Sp100 and the additional biomarker from their respective levels of expression or activity in a healthy mammalian subject is an indication or differential indication of a diagnosis of proliferative disease or disorder.

In another aspect, a method is provided for monitoring progression of proliferative disease or disorder in a mammalian subject suffering from that disorder. In this method the level of expression or activity of Sp100 in a biological sample from a mammalian subject having proliferative disease or disorder is measured and compared to the level of expression or activity of Sp100 of a temporally earlier biological sample of the same subject. In this method, an increased expression or activity level of the Sp100, compared to that in an earlier biological sample of the same subject is indicative of regression or improvement in the disorder. Conversely, a decrease in Sp100 in the later sample is indicative of progression or increase in severity of the disorder. As one embodiment, this method can be applied to a subject being treated for proliferative disease, e.g., cancer. In this circumstance, the method enables a determination of the efficacy of the treatment.

Conventional diagnostic assay methods for detection of protein, nucleic acid, or enzymatic activity may be selected by one of skill in the art given the teachings provided herein. For example, in one embodiment, a method of evaluating the probability of the presence of malignant cells can be performed in a group of cells freshly removed from a host. Such methods can be used to detect abnormal cell growth or replication, e.g., tumors, quantitate and monitor their growth, and help in the diagnosis and prognosis of proliferative disease. For example, a decrease in the level or activity of Sp100 from that of a standard is indicative of the presence of the proliferative disease, e.g., cancer.

Such methods involve comparing the amount of Sp100 quantitated in a sample from a subject being tested to a predetermined standard or cut-off value. A standard may correspond to levels quantitated for another sample or an earlier sample from the subject, or levels quantitated for a control sample, in particular a sample from a subject with a lower grade cancer. Levels for control samples from healthy subjects or cancer subjects may be established by prospective and/or retrospective statistical studies. Healthy subjects who have no clinically evident disease or abnormalities may be selected for statistical studies. Diagnosis may be made by a finding of statistically different levels of Sp100 compared to a control sample or previous levels quantitated for the same subject.

In other embodiments, the diagnostic methods use multiple markers for a proliferative disease. In one embodiment, a method analyzes a biological sample for the presence of Sp100 and other markers that are specific indicators of the proliferative disease or cancer. The methods described herein may be modified by including reagents to detect the markers or polynucleotides encoding the markers.

In one embodiment, the biomarker or its activity may be detected based on the level of a polynucleotide encoding one of the isoforms of Sp100 (or fragment thereof) in a sample. Techniques for detecting nucleic acid molecules such as polymerase chain reaction (PCR) and hybridization assays are well known in the art. Probes may be used in hybridization techniques to detect polynucleotides. The technique generally involves contacting and incubating nucleic acids obtained from a sample from a patient or other cellular source with a probe under conditions favorable for the specific annealing of the probes to complementary sequences in the nucleic acids (e.g. under stringent conditions as discussed herein). After incubation, the non-annealed nucleic acids are removed, and the presence of nucleic acids that have hybridized to the probe, if any, are detected. Nucleotide probes for use in the detection of polynucleotide sequences in samples may be constructed using conventional methods known in the art. The probes may comprise DNA or DNA mimics corresponding to a portion of an organism's genome, or complementary RNA or RNA mimics. The nucleic acids can be modified at the base moiety, at the sugar moiety, or at the phosphate backbone. DNA can be obtained using standard methods such as polymerase chain reaction (PCR) amplification of genomic DNA or cloned sequences. Computer programs known in the art can be used to design primers with the required specificity and optimal amplification properties.

A nucleotide probe may be labeled with a detectable substance such as a radioactive label which provides for an adequate signal and has sufficient half-life such as $^{32}P$, $^{3}H$, $^{14}C$ or the like. Other detectable substances that may be used include antigens that are recognized by a specific labeled antibody, fluorescent compounds, enzymes, antibodies specific for a labeled antigen, and luminescent compounds. An appropriate label may be selected having regard to the rate of hybridization and binding of the probe to the nucleic acids to be detected and the amount of nucleic acids available for hybridization. Labeled probes may be hybridized to nucleic acids on solid supports such as nitrocellulose filters or nylon membranes as generally described in Sambrook et al., 1989, Molecular Cloning, A Laboratory Manual (2nd ed.). The nucleic acid probes may be used to detect Sp100, preferably in human cells. The nucleotide probes may also be useful in the diagnosis of cancer, involving Sp100 in monitoring the progression of cancer, or monitoring a therapeutic treatment.

The detection of polynucleotides in a sample may involve the amplification of specific gene sequences using an amplification method such as PCR, followed by the analysis of the amplified molecules using techniques known to those skilled in the art. By way of example, oligonucleotide primers may be employed in a PCR based assay to amplify a portion of a polynucleotide and to amplify a portion of a polynucleotide derived from a sample, wherein the oligonucleotide primers are specific for (i.e. hybridize to) the polynucleotides. The amplified cDNA is then separated and detected using techniques well known in the art, such as gel electrophoresis.

In order to maximize hybridization under assay conditions, primers and probes employed in the methods of the invention generally have at least about 60%, preferably at least about 75% and more preferably at least about 90% identity to a portion of Sp100; that is, they are at least 10 nucleotides, and preferably at least 20 nucleotides in length. In an embodiment the primers and probes are at least about 10-40 nucleotides in length.

Hybridization and amplification reactions may also be conducted under stringent conditions as discussed herein. Hybridization and amplification techniques described herein may be used to assay qualitative and quantitative aspects of polynucleotide expression. For example, RNA may be isolated from a cell type or tissue known to express Sp100, and tested utilizing the hybridization (e.g. standard Northern analyses) or PCR techniques.

In another aspect, a method is provided employing reverse transcriptase-polymerase chain reaction (RT-PCR), in which PCR is applied in combination with reverse transcription. Generally, RNA is extracted from a sample using standard techniques and is reverse transcribed to produce cDNA. The cDNA is used as a template for a polymerase chain reaction. The cDNA is hybridized to primer sets which are specifically designed against a Sp100. Once the primer and template have annealed a DNA polymerase is employed to extend from the primer, to synthesize a copy of the template. The DNA strands are denatured, and the procedure is repeated many times until sufficient DNA is generated to allow visualization by ethidium bromide staining and agarose gel electrophoresis.

Amplification may be performed on samples obtained from a subject with suspected cancer, an subject who is not afflicted with cancer or has early stage disease or has aggressive or metastatic disease. The reaction may be performed on several dilutions of cDNA spanning at least two orders of magnitude. A statistically significant difference in expression in several dilutions of the subject sample as compared to the same dilutions of the standard, e.g., a non-cancerous sample or early-stage cancer sample may be considered positive for the presence of cancer.

In an aspect, a diagnostic method for monitoring or diagnosing proliferative disease in a subject involves quantitating a Sp100 isoform polypeptide (or a fragment thereof) in a biological sample from the subject comprising reacting the sample with antibodies specific for Sp100 which are directly or indirectly labeled with detectable substances and detecting the detectable substances.

In an aspect of the invention, a method for detecting or diagnosing cancer is provided comprising or consisting essentially of: (a) obtaining a sample of cells suspected of expressing a level or activity of an Sp100 polypeptide; (b) contacting said sample with antibodies that specifically bind Sp100 polypeptide under conditions effective to bind the antibodies and form complexes; (c) measuring the amount of Sp100 polypeptide present in the sample by quantitating the amount of the complexes; and (d) comparing the amount of Sp100 polypeptide present in the samples with the amount of Sp100 polypeptide in a control, wherein a change or significant difference or decrease in the amount or activity of Sp100 in the sample compared with the amount or activity in the control is indicative of a proliferative disease, e.g., cancer, stage of cancer, progression, aggressiveness and/or metastatic potential of the disease.

In one embodiment, the method for monitoring the progression of a proliferative disease in an subject, comprises: (a) contacting an antibody which binds to Sp100 polypeptide with a sample from the subject, so as to form a complex comprising the antibody and Sp100 in the sample; (b) determining or detecting the presence or amount of complex formation in the sample; (c) repeating steps (a) and (b) at a point later in time; and (d) comparing the result of step (b) with the result of step (c), wherein a difference in the amount of complex formation is indicative of disease, disease stage, progression, aggressiveness and/or metastatic potential of the proliferative disorder in the subject. The amount of complexes may also be compared to a value representative of the amount of the complexes from a subject not at risk of, or afflicted with cancer at a different stage.

Antibodies may be used in any immunoassay that relies on the binding interaction between antigenic determinants of Sp100 and the antibodies. Immunoassay procedures for in vitro detection of antigens in samples are also well known in the art. (See Sambrook et al, and other known publications for a general description of immunoassay procedures). Qualitative and/or quantitative determinations of Sp100 in a sample may be accomplished by competitive or non-competitive immunoassay procedures in either a direct or indirect format. Detection of Sp100 using antibodies can, for example involve immunoassays which are run in either the forward, reverse or simultaneous modes. Examples of immunoassays are radioimmunoassays (RIA), enzyme immunoassays (e.g. ELISA), immunofluorescence, immunoprecipitation, latex agglutination, hemagglutination, histochemical tests, and sandwich (immunometric) assays. Alternatively, the binding of antibodies to Sp100 can be detected directly using, for example, a surface plasmon resonance (SPR) procedure such as, for example, Biacore®, microcalorimetry or nano-cantilivers. These terms are well understood by those skilled in the art, and they will know, or can readily discern, other immunoassay formats without undue experimentation.

Antibodies specific for Sp100 may be labelled with a detectable substance and localised in biological samples based upon the presence of the detectable substance. Examples of detectable substances include, but are not limited to, the following: radioisotopes (e.g., $^3$H, $^{14}$C, $^{35}$S, $^{125}$I, $^{131}$I), fluorescent labels, (e.g., FITC, rhodamine, lanthanide phosphors), luminescent labels such as luminol; and enzymatic labels (e.g., horseradish peroxidase, beta-galactosidase, luciferase, alkaline phosphatase, acetylcholinesterase), biotinyl groups (which can be detected by marked avidin e.g., streptavidin containing a fluorescent marker or enzymatic activity that can be detected by optical or calorimetric methods), and predetermined polypeptide epitopes recognized by a secondary reporter (e.g., leucine zipper pair sequences, binding sites for secondary antibodies, metal binding domains, epitope tags). In some embodiments, labels are attached via spacer arms of various lengths to reduce potential steric hindrance. Antibodies may also be coupled to electron dense substances, such as ferritin or colloidal gold, which are readily visualized by electron microscopy.

One of the ways an antibody can be detectably labelled is to link it directly to an enzyme. The enzyme when later exposed to its substrate will produce a product that can be detected. Examples of detectable substances that are enzymes are horseradish peroxidase, beta-galactosidase, luciferase, alkaline phosphatase, acetylcholinesterase, malate dehydrogenase, ribonuclease, urease, catalase, glucose-6-phosphate, staphylococcal nuclease, delta-5-steroid isomerase, yeast alcohol dehydrogenase, alpha-glycerophosphate, triose phosphate isomerase, asparaginase, glucose oxidase, and acetylcholine esterase.

For increased sensitivity in an immunoassay system a fluorescence-emitting metal atom such as Eu (europium) and other lanthanides can be used. These can be attached to the desired molecule by means of metal-chelating groups such as DTPA or EDTA. A bioluminescent compound may also be used as a detectable substance. Examples of bioluminescent detectable substances are luciferin, luciferase and aequorin. Similarly a fluorescent protein, such as GFP, BFP etc, may be used as a reporter.

Indirect methods may also be employed in which the primary antigen-antibody reaction is amplified by the introduction of a second antibody, having specificity for the antibody reactive against Sp100. By way of example, if the antibody having specificity against Sp100 is a rabbit IgG antibody, the second antibody may be goat anti-rabbit IgG, Fc fragment specific antibody labeled with a detectable substance as described herein.

Methods for conjugating or labelling the antibodies discussed above may be readily accomplished by one of ordinary skill in the art.

In the context of the methods of the invention, the sample, binding agents (e.g. antibodies), or Sp100 may be immobilized on a carrier or support, such as, for example, agarose, cellulose, nitrocellulose, dextran, Sephadex, Sepharose, liposomes, carboxymethyl cellulose, polyacrylamides, polystyrene, filter paper, ion-exchange resin, plastic film, nylon or silk. The support material may have any possible configuration including spherical cylindrical or flat. Thus, the carrier may be in the shape of, for example, a tube, test plate, well, beads, disc, sphere, etc. The immobilized material may be prepared by reacting the material with a suitable insoluble carrier using known chemical or physical methods, for example, cyanogen bromide coupling. Binding agents (e.g. antibodies) may be indirectly immobilized using second binding agents specific for the first binding agent. For example, mouse antibodies specific for Sp100 may be immobilized using sheep anti-mouse IgG Fc fragment specific antibody coated on the carrier or support.

Aspects of the methods of the invention involve (a) reacting a biological sample from a subject with an antibody specific for Sp100 wherein the antibody is directly or indirectly labelled with enzymes; (b) adding substrates for the enzymes wherein the substrates are selected so that the substrates, or reaction products of the enzymes and substrates form fluorescent complexes; (c) quantitating Sp100 polypeptide in the sample by measuring fluorescence of the fluorescent complexes; and (d) comparing the quantitated levels to levels obtained for other samples from the subject patient, or control subjects.

In another aspect, a diagnostic composition or kit for diagnosing or differentially diagnosing the occurrence, stage or progression of proliferative disease or disorder in a mammalian subject is provided. In one aspect, the composition contains one or a plurality of polynucleotides immobilized on a substrate, wherein at least one polynucleotide is a genomic probe that hybridizes to Sp100 mRNA. In another aspect, the composition contains one or a plurality of PCR primer-probe sets, wherein at least one primer-probe set amplifies a polynucleotide (mRNA) sequence of Sp100. In another aspect, the composition contains one or a plurality of ligands, such as antibodies or fragments, wherein at least one ligand binds to Sp100 in a biological sample of a mammalian subject. In other embodiments, the other polynucleotides or other primer-probe sets or other ligands are designed to detect additional biomarkers. Such diagnostic compositions may also contain conventional labels which emit detectable signals when complexes with the Sp100 in the sample are formed.

Still other known methods and conventional, as well as commercial assays and components, may be employed in the practice of these methods for screening and diagnosis.

IV. EXAMPLES

The invention is now described with reference to the following examples. These examples are provided for the purpose of illustration only. The compositions, experimental protocols and methods disclosed and/or claimed herein can be made and executed without undue experimentation in light of the present disclosure. The protocols and methods described in the examples are not considered to be limitations on the scope of the claimed invention. Rather this specification should be construed to encompass any and all variations that become evident as a result of the teaching provided herein. One of skill in the art will understand that changes or variations can be made in the disclosed embodiments of the examples, and expected similar results can be obtained. For example, the substitution of reagents that are chemically or physiologically related for the reagents described herein are anticipated to produce the same or similar results. All such similar substitutes and modifications are apparent to those skilled in the art and fall within the scope of the invention.

The inventors provide herein the only in vitro model that allows study of the progressive events that occur during the transition of a normal diploid cell to an aggressively tumorigenic cell, and provides the opportunity to identify the processes that drive the various intermediate stages.

As demonstrated in the examples below, suppression of expression of the four major Sp100 isoforms (isoforms 1 to 4 in Table I) leads to immortalization of normal human neonatal fibroblasts. This immortalization is preceded by the transient expression of embryonic stem cell (ESC) markers, is accompanied by a mesenchymal to epithelial trans-differentiation event (MET), and results in an acquired capacity to form tumors in nude mice. Using selective Sp100 isoform-knockdown approaches, we show that normal human diploid fibroblasts with reduced Sp100 levels rapidly senesce. Subsequently, small rapidly dividing Sp100 minus cells emerge from the senescing fibroblasts and are found to be highly tumorigenic in nude mice. The derivation of these tumorigenic cells from the parental fibroblasts is confirmed by micro-satellite analysis. The small rapidly dividing Sp100 minus cells now also lack ND10/PML bodies, exhibit genomic instability and p53 cytoplasmic sequestration. They also have activated MYC, RAS and TERT pathways and express mesenchymal to epithelial (MET) trans-differentiation markers. Reintroduction of expression of only the Sp100A isoform is sufficient to maintain senescence and to inhibit emergence of the highly tumorigenic cells. Global transcriptome studies, quantitative PCR and protein studies as well as immunolocalization studies during the course of the transformation reveal that a transient expression of stem cell markers precedes the malignant transformation. These results identify a role for Sp100 as a tumor suppressor, and as a means for generating somatic cells that can be reprogrammed into pluripotent stem cells.

Example 1: Materials and Methods

A. Cells and Treatments.

Human embryonic kidney 293 (HEK293), 293T and human diploid foreskin fibroblast (BJ cells obtained from ATTC at population doubling of 23) were maintained in Dulbecco's modified Eagle medium (DMEM) supplemented with 10% FCS and 1% antibiotics. All cells were grown at 37° C. in a humidified 5% $CO_2$ atmosphere. Certain cells cultures were treated with 1000 U/ml of IFNβ for 18 hours, as indicated.

B. Sp100 Knock-Down.

For lentiviral pLKO.1 vector-based knock-down, A11 (clone TRCN000019224), B1 (clone TRCN000019226) and A7 (clone TRCN000019227) were purchased from Open BioSystems (Huntsville, Ala.). To create S2 knock-down of Sp100 we used a previously characterized construct based on the pLKO.1 vector, as described in Everett, R D et al, 2008 J. Virol., 82:2661-72, incorporated by reference herein. The protocol followed was as described previously in Negorev D G, et al, 2009 J. Virol., 83:5168-80, incorporated by reference herein. Passage number after transduction with lentivirus is used since the cell numbers varied considerably per confluent culture dish specifically during the onset of senescence. Population doubling time is therefore substantially higher for the BJsm cells than BJV or BJ-S cells.

C. Indirect Immunofluorescence.

The protocol of Negorev et al, 2009, cited immediately above, was followed with minor modifications. Cells were analyzed using a Leica confocal laser-scanning microscope. ND10 bodies were visualized using the following antibodies: monoclonal antibody (mAb) PG-M3 recognizes PML (Santa Cruz Biotechnology, Santa Cruz, Calif.) (1:500 dilution), rabbit antibody AB1380 against Sp100 (Chemicon International, Temecula, Calif.) (1:1000 dilution).

D. Mammalian Cell Transfection and Reporter Assays.

BJ cells or 293T cells were cultured in DMEM plus 10% FCS and were transfected with plasmids using the Lipofectamine 2000 (Invitrogen) reagent according to the manufacture's protocol. In vitro luciferase assays were performed as described previously in Negorev et al, 2009, cited immediately above. The GFP-tagged Sp100 constructs were prepared as described in Negorev D G et al, 2006 J Virol, 80:8019-29, incorporated by reference herein.

E. Western Blotting.

Total cellular protein extract was prepared as described in Negorev et al, 2009, cited above. The following antibodies were applied: rabbit anti-Sp100 antibody AB1380 (1:30,000 dilution), rabbit anti-Daxx antibody 2133 (1:300 dilution) (25), mAb anti-GFP B-2 (1:2,000 dilution) (Santa Cruz Biotechnology, Santa Cruz, Calif.), and mAb anti-tubulin (1:10,000 dilution) (Sigma, St Louis, Mo.).

F. RT-PCR and Quantitative PCR.

Total cellular RNA was prepared using Trizol reagent (Life Technologies, Rockville, Md.) as described in Negorev et al, 2009, cited above. PCR products were run on 2% agarose gels. For quantitative real-time-PCR (qRT-PCR) analysis, 2.5 µg of total RNA were used to synthesize cDNA using the Superscript First-Strand Synthesis System for RT-PCR (Invitrogene) according to the manufacturer's protocol. 40-cycle qRT-PCR products from 50 ng cDNA and 250 nM each of gene-specific primers (see Table 2))) were detected using SYBR green and standard thermal cycler conditions in 7900HT Fast Real Time PCR System (ABI). Each sample was run in triplicate on 384-well plate. Endogenous GAPDH expression was used for internal normalization.

G. Genotype Determination.

Genomic DNA was prepared from BJ, BJsm and 293T cells using DNeasy Blood and Tissue kit (QIAGEN). Genotyping was performed on genomic DNA using the Identity Mapping Kit (Cornell) according to the manufacture's protocol. Briefly, 60 ng of genomic DNA was used per PCR reaction with a set of five highly polymorphic tetra-nucleotide microsatellites, FES/FPS, vWA31, D22S417, D10S526, and D5S592 for genotype determination. Amplified products were analyzed for fragment size on an Applied Biosystems 3130x1 Genetic Analyzer.

H. Individual TaqMan® miRNA qRT-PCR.

Reverse transcription was conducted using TaqMan® microRNA reverse transcription kit (ABI) with 100 ng total RNA and Human Multiplex RT primer pool v1.0 in 15 ml reaction volume. qRT-PCR reactions with 3-fold diluted cDNAs were assembled in 384-well plates in triplicate and assayed in the ABI 7900HT Fast Real-Time PCR System. The individual assay IDs were 002307 for hsa-let-7a and 002405 for hsa-let-7c, respectively. miRNA expression was normalized by small nucleolar RNAs (RNU44 and RNU48) measured in each individual sample using individual control TaqMan® assays, and fold changes were calculated using the delta-delta Ct method as described in Livak K J et al 2001 Methods 25:402-8, incorporated herein by reference.

I. Microarrays.

We performed microarray analysis of mRNAs expression in BJV, collected at p15; BJ-S, collected at p11; and BJsm cells, collected at p57, when no cells with BJ-S morphology could be found in the population of BJsm cells. In addition samples were treated for 24 h with 1000 units/ml IFNβ. IFNβ was included as it allowed the isolation of Sp100 dependent gene expression. A constant amount (400 ng) of total RNA was amplified, as recommended by Illumina. Samples were hybridized to the Illumina WG-6v2 human whole genome bead arrays. Illumina BeadStudio v.3.0 software was used to export expression levels and to determine p-values for each probe for each sample. Arrays were normalized between each other and filtered to remove non-informative probes. A probe was called non-informative if it had detection p-value>0.05 in all samples or if maximum ratio between expression values was not at least 1.2 between at least two samples.

J. Analysis

Data for 18 samples (6 groups, 3 replicates) was tested for differentially expressed genes using one-way ANOVA analysis with significance set to p-value<0.05. False Discovery Rate was calculated according to Storey J D 2003 Proc Natl Acad Sci USA, 100:9440-5. The heat maps were generated using 2-way hierarchical clustering using Euclidean distance to cluster samples/conditions and Spearman correlation distance to cluster genes. Pathway analysis was carried out using Ingenuity Pathways Analysis software, using Ingenuity Core Analysis (IPA 6.0, Ingenuity® Systems) with Benjamini-Hochberg multiple testing corrected p-value<0.01 as a significance threshold. Fisher exact test was used to test significance of an enrichment of genes with specific annotation (transcription factor target, biological process, function, etc.) in a list with significance threshold set to p-value<0.05. Our microarray profiling data can be found at the Gene Expression Omnibus (GEO) database under accession GSE20613, incorporated by reference.

Example 2: Targeting Sp100 Expression in Human Fibroblasts

ShRNA-directed Sp100 suppression was used to explore the role of Sp100 and its isoforms in human diploid fibroblast growth. To target the various isoforms, human diploid fibroblasts (BJ cells) were transduced with two pools of lentivirus expressing shRNA. Viruses A7 and S2 targeted all isoforms; viruses A11 and B1 targeted only the SAND-domain-containing isoforms (Gibson T J et al, 1998, Trends Biochem Sci 23(7):242-4) (see FIG. 1A). Control BJ cells were transduced with empty vector and named BJV cells. Transduced cells were selected with 0.5 µg/ml puromycin for 3 days followed by serial passaging.

Suppression of Sp100 isoform expression was confirmed by quantitative RT-PCR (FIG. 1B). BJ cells transduced to suppress only SAND-containing Sp100 isoforms are designated BJ-SAND cells. As expected expression of the Sp100A isoform, which lacks a SAND domain, is unaffected in the BJ-SAND cells and retains its sumoylated modifications and its interferon inducibility (FIG. 1C, lane 7 and 8). All isoforms are suppressed in BJ-S cells (FIG. 1C, lane 3 and 4), a suppression that cannot be overcome by interferon activation.

Figure 2:
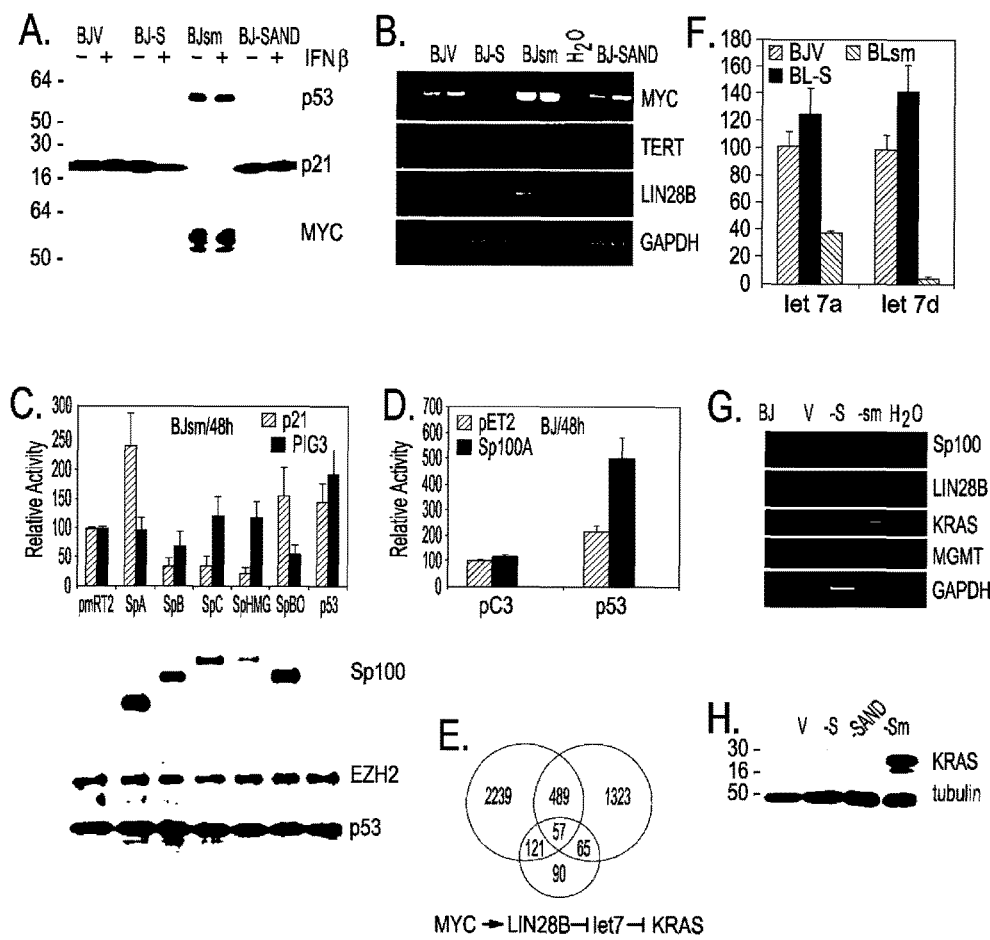
FIG. 2A-2H show activation of several oncogenic pathways in BJsm cells.

The vector-transduced BJV cells continued to actively proliferate and did not senesce within the time fame investigated, in agreement with previous observations (Stewart S A, et al, 2003 Nat Genet 33(4):492-6). By contrast, both BJ-S and BJ-SAND cells proliferated slowly after shRNA transduction and showed enhanced senescence associated (SA)-β-galactosidase staining between passages 10-13 post-transduction. Cultures at this point were comprised of large flat cells. The BJ-SAND cells became multinucleated, showed intense staining and stopped proliferation at passage 16 post-transduction (See FIG. 2, panels A-I of U.S. Provisional patent application No. 61/565,298 and Negorev et al 2010, Cancer Research, 70(23):9991-10001, are photomicrographs showing the characterization of BJV, BJ-SAND and BJsm cells. Panel 2A depicts senescence-associated acidic β-galactosidase staining of BJV cell line showing low staining in BJV cells at passage 24 (p24). Panel 2B depicts senescence-associated acidic β-galactosidase staining of BJsm cell line showing complete loss of its expression in BJsm cells with changed morphology at passage 25. Panel 2C depicts senescence-associated acidic β-galactosidase staining of BJ-SAND cells, showing high staining of BJ-SAND cells at passage 16 post transduction. Panel 2D is immunofluorescence microscopy of BJV cell line stained with Sp100 and PML antibodies, showing perfect colocalization in BJV cells. Panel 2E is immunofluorescence microscopy of BJsm cell line stained with Sp100 and PML antibodies, showing the loss of all Sp100 and most PML aggregates, i.e., ND10/PML bodies in BJsm cells at passage 25. Panel 2F is immunofluorescence microscopy of BJ-SAND cell line stained with Sp100 and PML antibodies, showing apparently normal staining in BJ-SAND cells often with increased PML staining at passage 16. Panel 2G is immunofluorescence microscopy of BJV cell line, showing that DNA break recognition indicator γH2AX foci were found only occasionally in BJV cells, rarely many. The image selected has one of these cell phenotypes displayed. Panel 2H is immunofluorescence microscopy of BJ-SAND cell line, showing one or two DNA break recognition indicator γH2AX foci per nucleus. Panel 2I is immunofluorescence microscopy of BJsm cell line, showing high numbers of DNA break recognition indicator γH2AX foci per nucleus in all BJsm cells.

Example 3: Rapid Emergence of Immortalized Cells in Cultures with Suppressed Expression of all Sp100 Isoforms During the onset of senescence, which occurs between passages 11 to 15 post-transduction, smaller rapidly growing cells emerge (designated BJ small or BJsm). See FIG. 1D in Negorev et al, 2010, cited above, which shows six photomicrographs showing the transition of BJ-S cells to small BJsm cells over several passages. Panel BJ-S/sm shows small cells aligned with dendrites of fibroblast. These small cells are initially tightly associated with dendritic extensions of the large flattened fibroblasts (BJ-S/sm p13). This emergence was followed by the development of clones with a cobble stone-like morphology and strong self-adherence (BJsm p15) and FIG. 2, panel B (depicts senescence-associated acidic β-galactosidase staining of BJsm cell line showing complete loss of its expression in BJsm cells with changed morphology at passage 25 in Negorev et al, 2010, cited above). As determined by z-axis confocal microscopy, BJsm cells have approximately five times the height as the flat BJV and BJ-S cells (data not shown). These BJsm cells arise multi-focally in each culture and rapidly outgrow the BJ-S cells within 3-4 passages. FIG. 1, panel E is a graph depicting the growth curves of BJsm cells in comparison with parental BJ and HEK293, in Negorev et al, 2010, cited above, and compares the growth rate of BJV, BJsm cells with HEK293 cells, a fast growing cell line maintained in the laboratory, which also lacks Sp100. These HEK293 cells do not adhere to each other. BJsm cells grow substantially faster than parental BJ fibroblasts and faster than HEK293 cells and they do not express senescence-associated SA-β-galactosidase (See FIG. 2, panel B in Negorev et al, 2010, cited above). These apparently immortalized cells arose in multiple, independently derived cultures of BJ-S cells, and have gone through more than 100 passages. BJsm cells lack all mRNA Sp100 isoforms, as determined by qRT-PCR (FIG. 1B herein), and exhibit a significant reduction in PML and Daxx proteins (FIG. 1C, lane 5 and 6, herein). Concomitantly, ND10/PML bodies are reduced from >20 per nucleus in BJ-S cells to approximately one per nucleus in BJsm cells (FIG. 2, panel E in Negorev et al, 2010, cited above). These results provide evidence that loss of Sp100 leads to rapid immortalization and morphologic transformation of primary human fibroblasts.

Previous observations had shown that elevated expression of the minor PML IV isoform induces senescence (Bischof O et al., 2002 EMBO J., 21(13):3358-69). Using qPCR analysis we found that expression of PML IV mRNA increased substantially in BJ-SAND as one might have expected. But surprisingly it is also increased in the fast growing BJsm cells. However, no apparent increase of PML protein was detected in BJ-SAND cells using Western blots (FIG. 1B herein).

We therefore measured the relative expression level of the major PML I isoform by qRT-PCR analysis in the BJ, BJ-S, BJsm and BJ-SAND cell lines. We found that PML I transcript levels are equivalent to levels in all cell lines except the transformed BJsm where it is substantially increased (4 fold) (data not shown). The apparently normal PML I expression in BJ, BJ-S and BJ-SAND is in contrast to high expression of PML IV mRNA in senescing BJ-SAND (FIG. 1B herein), demonstrating that a change in the PML splicing pattern has occurred. The increased expression of PML IV and PML I transcripts in BJsm cells should have no consequence as all PML protein isoforms are not detected (FIG. 1B).

To exclude the possibility that immortalization and transformation are the result of lentivirus integration, we repeated the infection and serial passaging experiment several times. In 5/8 independent repeats we observed the appearance of BJsm cells, but never observed immortalization of BJ cells transduced with vector only lentiviruses or with lentiviruses suppressing only SAND-domain containing Sp100 isoforms. Thus immortalization as a result of off-target or integration events is highly unlikely.

We also addressed the concern that the transformed BJsm cells may have been derived from some low level of contaminating cells in the original fibroblast cultures. We initially excluded the 293T cells, used to produce the lentiviruses, as a possible contaminant by testing BJsm cells for the presence of large T-antigen expressed in 293T cells. No T-antigen expression was detected in either the fibroblasts or the emerging transformed cell (data not shown). The identity of the emerging cells as being derived from the parental BJ fibroblasts and not from some contaminant was further confirmed by micro satellite comparative analysis of the parental BJ cells, the emergent transformed BJsm cells and the 293T cells used to prepare the shRNA vectors. We found a perfect identity of the micro-satellite markers detected in the fibroblast and transformed cells, while the 293 cells exhibited an altered panel of markers. This further eliminates 293 cells as a source of the emerging transformed cells. More importantly this observation confirms the derivation of the BJsm transformed cells from the parental BJ fibroblasts (see Table 3). Table 3 lists the cell lines BJsm, 293T, BJV using the listed markers for a microsatellite analysis. All 5 markers produced similar fragment sizes for BJ and BJsm cells, indicating that BJsm cells are of BJ origin.

TABLE 3

| SAMPLE | MARKER | SIZE 1 | SIZE 2 | SIZE 3 |
|---|---|---|---|---|
| BJsm | D10S526 | 234 | 238 | 242 |
| BJsm | D5S592 | 173 | 177 | 182 |
| BJsm | D22S417 | 180 | 184 | |
| BJsm | FES-FPS | 216 | 220 | |
| BJsm | vWA31 | 147 | 151 | 155 |
| 293T | D10S526 | 196 | 200 | 204 |
| 293T | D5S592 | 165 | 173 | 177 |
| 293T | D22S417 | 180 | 184 | |
| 293T | FES-FPS | 216 | 220 | |
| 293T | vWA31 | 147 | 155 | 160 |
| BJV | D10S526 | 234 | 238 | 242 |
| BJV | D5S592 | 173 | 177 | 182 |
| BJV | D22S417 | 180 | 184 | |
| BJV | FES-FPS | 216 | 220 | |
| BJV | vWA31 | 147 | 151 | 155 |

Example 4: BJSM Cells can Form Tumors in Nude Mice

The immortalized BJsm cells were also demonstrated to form spheres in low or serum free medium (data not shown). When such spheres were transferred back to medium with 10% FBS, all cells reformed monolayers, indicating that these cells have properties of tumor-spheres. We then determined whether the BJsm cells had the potential to form tumors in nude mice. Subcutaneous injection of $1\times10^6$ BJsm cells resulted in large tumors after 6 weeks; whereas, mice injected with BJ and BJV cells were tumor free even after 3 months. HeLa cells were used as a positive control (See FIG. 1, panel F in U.S. provisional patent application No. 61/565, 298 and Negorev et al, 2010, cited above, which are photomicrographs (a) through (f) showing tumor formation in nude mice. Cells injected are indicated at the respective side of the mouse (a and b). Size difference of tumors formed with equal number of cells injected (c and d) and H&E staining of tumors (e and f)). Histological examination of BJsm derived tumors showed tightly packed cells with a nucleus/cytoplasm ratio significantly higher than those derived from HeLa cells -. We found no evidences of differentiation into different cell types. Thus, while suppression of just the Sp100 isoforms with a SAND domain, leads to accelerated senescence of normal human fibroblasts, complete suppression of all Sp100 isoforms (including Sp100A) leads to the emergence of immortalized cells which can form tumors in nude mice.

Example 5: Further Characterization of the Transformed BJSM Cells

We examined the molecular basis of the immortalization and transformation in BJsm cells. A hallmark of dividing cells that bypass replicative senescence is genomic instability and DNA damage (Mathon N F, Lloyd A C. 2001 Nat Rev Cancer, 1(3):203-13). DNA break recognition is known to activate the ATM kinase followed by γH2AX phosphorylation (Rogakou E P et al, 1998 J Biol Chem 273(10):5858-68). Analysis of γH2AX foci showed that most BJV cells had no γH2AX foci, a few had 2-5 foci and only a very few had over a hundred foci (a selected image, FIG. 2, panel G in U.S. provisional patent application No. 61/565,298 and Negorev et al, 2010, cited above, shows all three phenotypes). BJ-S cells also exhibited no more than five foci per cell (see FIG. 2, panel H in U.S. provisional patent application No. 61/565,298 and Negorev et al, 2010, cited above). However, almost all BJsm cells were positive for a large number of γH2AX foci (see FIG. 2, panel I in U.S. provisional patent application No. 61/565,298 and Negorev et al, 2010, cited above). Thus a high level of DNA breaks occur in BJsm cells suggesting pronounced genomic instability in cells lacking Sp100.

In previous studies, BJ cells have been transformed by activation of the MYC and RAS pathways and by suppression of p53 and RB (Hahn W C et al, 1999 Nature, 400(6743):464-8). We examined their mRNA expression levels in the BJsm cells. While MYC and RAS were found to be upregulated, surprisingly we found p53 expression to also be highly upregulated in BJsm cells. Exhaustive sequencing of p53 transcripts from BJsm cells did not find any inactivating mutations.

However, we also found that the p53 target gene $p21^{CIP1}$ was not expressed (FIG. 2A), suggesting that p53 was likely functionally inactivated, perhaps due to cytoplasmic sequestration. To investigate this possibility, we immuno-stained BJV, BJ-S and BJsm cells with anti-p53 and anti-HSP70 antibodies. When stained with anti-p53 antibodies, p53 is barely recognizable in BJV cells. BJ-S cells have increased p53 mostly in cytoplasm, whereas BJsm cells have increased p53 in large aggregates in the cytoplasm, most likely representing accumulation of misfolded p53. Immune staining for anti-HSP70 antibodies found p53 aggregated with the highly induced HSP70 only in the cytoplasm of the BJsm cells. This suggests that although p53 transcription is high, a large part of wt p53 is inactivated due to its sequestration in the cytoplasm with HSP70 (data not shown).

Example 6: Sp100 as a Tumor Suppressor

To further demonstrate that Sp100A is acting as a tumor suppressor, we transfected BJsm cells with a vector expressing an RFP-tagged Sp100A and followed the growth of the transfected cells using fluorescence microscopy. We found that the RFP-expressing BJsm cells did not divide and rapidly disappeared from the culture. To determine whether this phenomenon might be due to reactivation of the wild type p53, we measured the response of a p53 activated $p21^{CIP1}$ luciferase reporter plasmid to the introduction of the RFP tagged Sp100A expression vector. We found that ectopic Sp100A expression enhanced activity of the $p21^{CIP1}$ promoter, while the isoforms with SAND domains suppressed $p21^{CIP1}$ expression.

To determine whether this suppression might be due to the DNA binding capacity of the SAND domain, we made a single amino acid mutation (W-Q) in the DNA binding site of the suppressive Sp100B isoform yielding the mutant Sp100BQ. Indeed, transfection of BJsm with the Sp100BQ mutant reversed the suppression. Moreover, the effect of Sp100BQ was specific to the $p21^{CIP1}$ promoter; we did not see any effect on the PIG3 promoter driven reporter. However both promoters were responsive to transfection of p53 (FIG. 2C). These results provide evidence that the tumor-suppressive p53 functions are inactivated by its sequestration in the cytoplasm in the absence of the Sp100A isoform.

The different Sp100 isoforms can interact with each other. Shifting the isoform balance in favor of Sp100A by reducing the SAND domain containing isoforms leads to early senescence.

We then examined the effects of changing the balance of the Sp100 isoforms by increasing the level of Sp100A in wild type BJ cells. Contrary to the BJsm cells, BJ cells survive the introduced RFP-Sp100A expression. However, the induction of $p21^{CIP1}$ is low to non-existent (FIG. 2D). Since normal fibroblasts have very little p53 (none detected by western blot; see FIG. 2A), we tested whether the lack or presence of very low amounts of p53 can account for these negative results. When we transfected BJ cells with p53 alone, we doubled the $p21^{CIP1}$ reporter signal likely due to the residual amount of Sp100A present in the BJ fibroblasts. Co-transfection of p53 and Sp100A, however, substantially increased $p21^{CIP1}$ promoter activity to 5 times the control level (FIG. 2D). This shows that Sp100A alone does not directly activate $p21^{CIP1}$ but synergizes with p53 in activating the $p21^{CIP1}$ promoter.

Another hallmark of cells that bypass replicative senescence is the re-expression of telomerase which counteracts the progressive shortening of telomeres (Bodnar A G et al, 1998 Science, 279(5349):349-52). We found a robust induction of TERT mRNA in BJsm cells, consistent with the by-pass of senescence, but not in the BJV or BJ-S cells (FIG. 2B). Since the expression of TERT is regulated by MYC, we also tested MYC expression in all BJ cell lines. We found that the MYC gene was highly expressed in BJsm cells at both the mRNA and protein levels (FIGS. 2A and 2B), suggesting that MYC expression is also deregulated in BJsm cells. Together these data show that Sp100 knock-down resulted in the deregulation of p53 and MYC, which in turn contributed to the transformation of BJsm cells.

We compared gene expression patterns in BJV, BJ-S, and BJsm cells using Illumina microarrays. We also evaluated gene expression as a function of the interferon response of each of the 3 cell types as this function is often altered in transformed cells (Park M S et al, 2003 J Virol., 77(17): 9522-32). We identified transcription factors that were differentially expressed between the transformed BJsm cells and the BJV, BJ-S cells. We identified 261 transcription factors with significantly changed expression levels in BJsm cells in this comparison. The top 50 genes that showed the biggest difference are shown in FIG. 4A. Among significantly induced transcriptional factors in BJsm cells, were LEF1 and its target MYC and E2F2 that support fast proliferation of those cells. Two of the factors LEF1 and E2F2, upregulated in BJsm cells support accelerated proliferation of cells and in addition, LEF1 targets MYC which is also up-regulated in these cells.

We also compared the expression of known MYC target genes in the 3 cell lines. We found that 53% of 333 core MYC regulated genes (Chandriani S et al, 2009 PLoS One, 4(8):e6693) were highly induced in BJsm cells. FIG. 4B shows expression of 50 of those genes selected by maximum fold change. An additional comparison with the more extensive MYC target gene database (Chang T C et al. 2009 Proc Natl Acad Sci USA, 106(9):3384-9) revealed that 546 of 1934 MYC-regulated genes were also induced in BJsm cells (FIG. 2D). The deregulation of many of these target genes compared to BJV cells, including expression of LIN28B (a known suppressor of the let7-RAS pathway), was confirmed by RT-PCR (partially shown in FIGS. 2B and 2F). Since LIN28B (or LIN28) has been shown to determine the level of mature let-7 in cancer cells, we used qRT-PCR to confirm the suppression of let-7a and let-7d levels in BJsm cells (FIG. 2F). One of the known targets of let-7 is KRAS. In agreement with suppression of let-7, we found the induction of KRAS at the protein (FIG. 2H) but not at the mRNA level in BJsm cells (FIG. 2G). This observation is consistent with the removal of a translational block. This increase in KRAS protein was further supported by our microarray data which showed that expression of 503 genes associated with an activated KRAS signature (Jeong S H et al, 2009 Exp Mol Med, 41(12):912-8; Chang J T et al, 2009 Mol Cell, 34(1): 104-14) also changed significantly in BJsm cells. The top 50 significantly changed genes are shown in FIG. 4C. KRAS is frequently activated through mutations that correlate with MGMT suppression. We found a reduction of MGMT mRNA levels in BJsm cells (FIG. 2G). Together these results provide evidence that in addition to p53 and MYC, the RAS oncogenic pathway is deregulated in BJsm cells. miRNA profiles on these cells are anticipated to play an important role.

Example 7: Expression of Embryonic Stem Cell Markers in BJSM Cells

Further analysis of the microarray data also revealed evidence for expression of embryonic stem cell markers in BJsm cells. We found that 325 genes reported to belong to the embryonic stem cell (ESC) expression program (Wong D J et al, 2008 Stem Cell, 2(4):333-44) were significantly upregulated in BJsm compared to BJ-S cells in our microarray studies. However, the canonical POU5F1, NANOG, SOX2, and KLF4 reprogramming factors (RFs) (Okita K et al, 2007 Nature, 448(7151):313-7; Wernig M et al, 2007 Nature, 448(7151):318-24; Yu J et al, 2007 Science, 318 (5858):1917-20) were not found to be activated in these cells. To determine whether these RFs were only expressed transiently during the transformation process, we used semi-quantitative RT-PCR to examine expression of these genes in BJ-S cells at different passages spanning the process of their transformation to BJsm cells.

Figure 4:
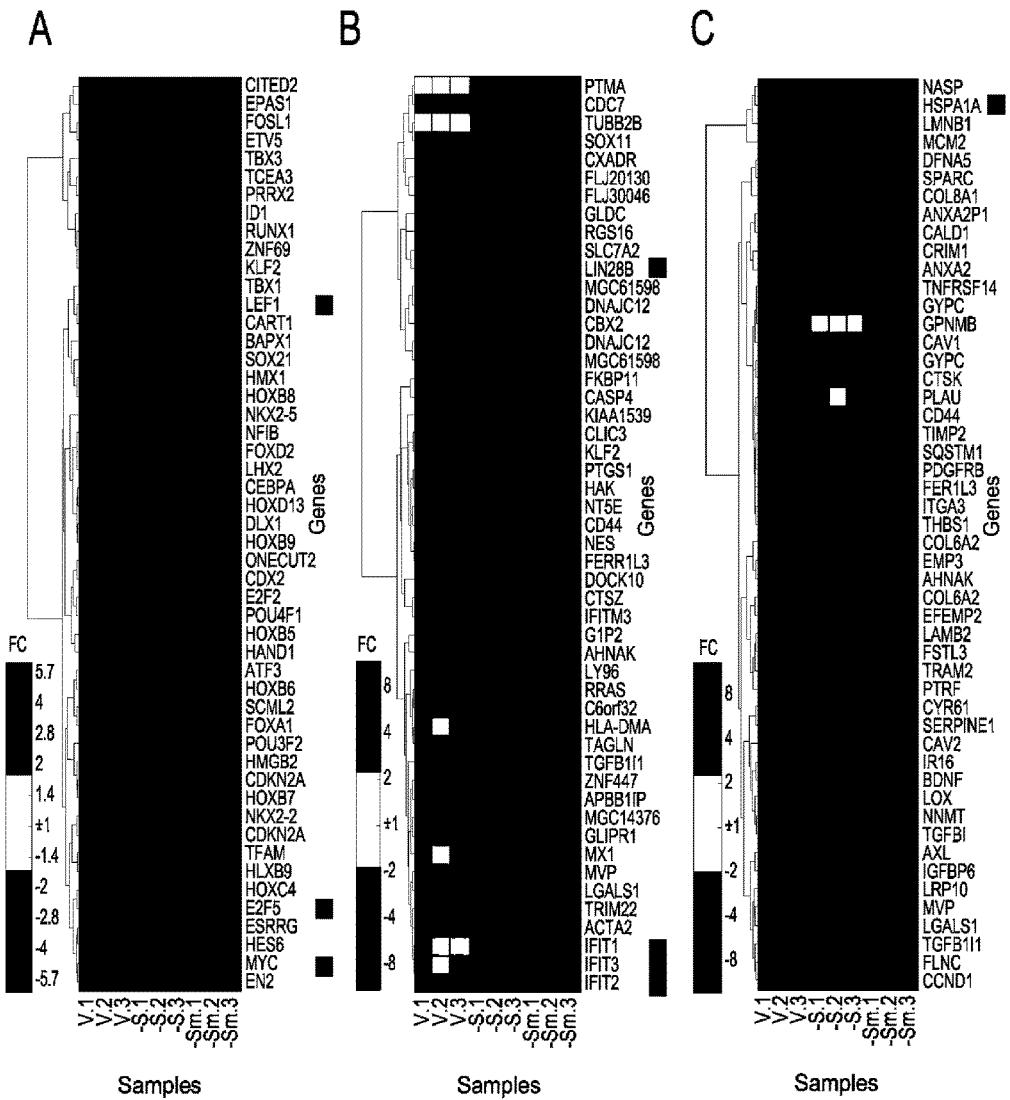
FIG. 4A is a microarray analysis showing the top 50 of 261 transcription factors with significantly changed expression levels in BJsm cells when compared with the BJV and BJ-S cells.
FIG. 4B is a microarray analysis showing expression of the top 50 of 333 known MYC target genes in the 3 cell lines. 53% of 333 core MYC regulated genes were highly induced in BJsm cells. Expression of 50 of those genes selected by maximum fold change is shown.
FIG. 4C is a microarray analysis showing expression of the top 50 of 503 genes associated with an activated KRAS signature that changed significantly in BJsm cells.

U.S. provisional patent application No. 61/565,298 and Negovev et al 2010, cited above, show in FIGS. 4A-4H of that BJsm cells temporally pass through an ESC-like stage. FIG. 4, panel A is an RT-PCR analysis of appearance of RFs during the transition time from BJ-S cells to BJsm cells. Passages number after transduction is indicated on top. FIG. 4, panel B is a Western blotting of SOX2 and various other proteins, involved in ESC biology, during the transition time from BJ-S cells to BJsm cells. FIG. 4, panel C is immunofluorescence microscopy of BJV cell line during BJ-S/sm transition stained with PML and SOX2 antibodies. The cells are devoid of SOX2. FIG. 4, panel D is immunofluorescence microscopy of BJ-S cell line stained with PML and SOX2 antibodies. BJ-S cells are devoid of SOX2 at p11. FIG. 4E is immunofluorescence microscopy of BJ-S cells at passage 12 stained with PML and SOX2 antibodies. The first large cells with SOX2 staining are devoid of aggregated PML (F), whereas senescing cells have an overabundance of PML (BJ-S p12). FIG. 4, panel F is immunofluorescence microscopy of BJ-S/sm cells at passage 13 stained with PML and SOX2 antibodies. At the BJ-S/sm transition (p13) many cells stain for SOX2 and have one or two PML aggregates. FIG. 4, panel G is an immunofluorescence microscopy of BJsm cells at passage 14 stained with PML and SOX2 antibodies. At p14 a few cells exhibit high SOX2 staining and only a few large cells are left. FIG. 4, panel H of the cited documents shows immunofluorescence microscopy of BJsm cells at passage 22 stained with PML and SOX2 antibodies. SOX2 is lost by p22.

Expression of POU5F1 and SOX2 mRNA was found to transiently increase at passages 13-15, with expression being suppressed again by passage 22. NANOG mRNA was transiently increased, only at passage 14-15, while KLF4 mRNA increased at the earliest tested, passage 11 (see FIG. 4, panel A in U.S. provisional patent application No. 61/565, 298 and Negorev et al, 2010, cited above). Expression of all RFs was undetectable by RT-PCR after passage 22 concordant with the microarray data. Significantly, the appearance of SOX2, POU5F1 and NANOG mRNA coincides with complete suppression of Sp100 mRNA.

We also confirmed the expression of individual RFs in BJ-S cells by immune-fluorescence microscopy. Nuclear SOX2 protein staining appeared at passage 13 (see FIG. 4, panels C-H in U.S. provisional patent application No. 61/565,298 and Negorev et al, 2010, cited above), in complete agreement with RT-PCR and Western blotting analysis (FIG. 4, panels A and B), and increased with passage number. Importantly, SOX2 is expressed early in the large, flat BJ-S cells before overt transformation is evident (FIG. 4, panel E in U.S. provisional patent application No. 61/565, 298 and Negorev et al, 2010, cited above). SOX2 expression was never observed in BJV cells expressing Sp100. We observed similar expression patterns for POU5F1 and NANOG (data not shown). These results suggested that BJ cells transiently express markers consistent with an ESC-like state, before progressing to KRAS-mediated transformation.

Example 8: Identification of a Mesenchymal-Epithelial Transition (MET) Profile

Figure 3:
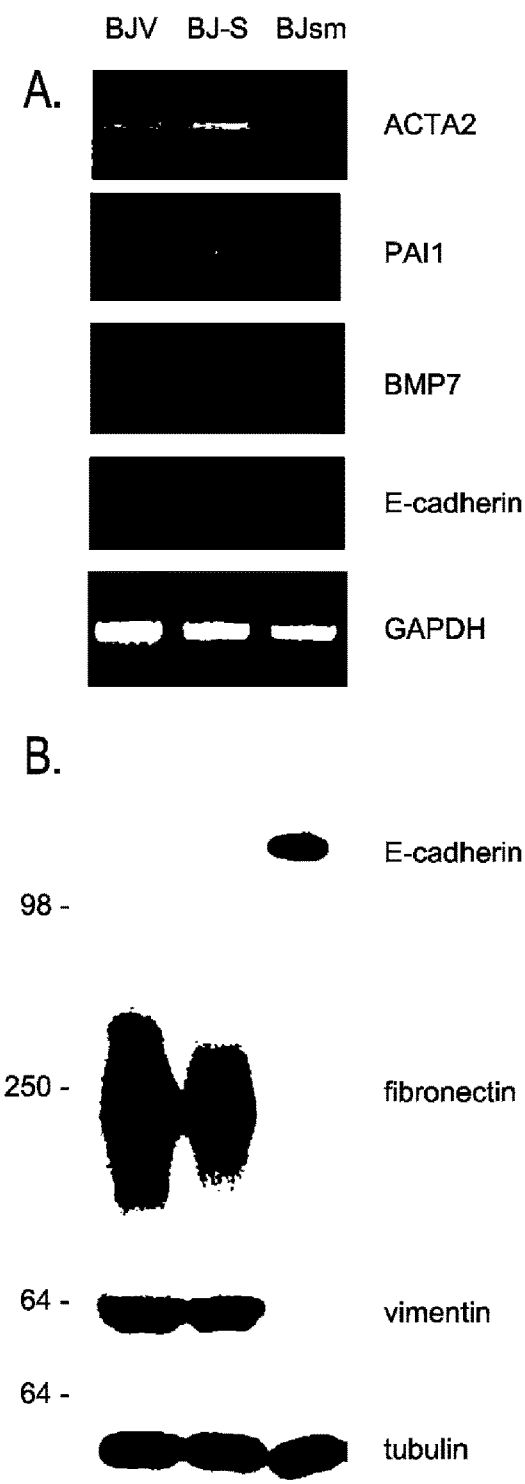
FIGS. 3A-3B provide evidence for a mesenchymal-epithelial transition from BJ-S to BJsm cells.

We have indicated above that BJsm cells form a cobblestone pattern in culture, that they are tightly attached to each other and that they form aggressive tumors with epithelial morphology in vivo. The morphological changes observed during the BJ-S to BJsm transition suggest a mesenchymal-epithelial trans-differentiation event has occurred. Analysis of the microarray data focused on this possibility showed there was a suppression of transcription factors required for the mesenchymal phenotype: TWIST1, SNAI1, SNAI2, JUB (Ajuba) already evident in BJ-S cells, and that BJsm cells exhibited an additional suppression of the mesenchymal phenotype markers: CDH2 (N-cadherin), S100A4 (FSP1), VIM (vimentin), FN1 (fibronectin) and SERPINE1 (PAI-1). Induction of the expression of epithelial markers ACTA2 (aortic smooth muscle actin) and CDH1 (E-cadherin) was confirmed in BJsm cells by RT-PCR. E-cadherin induction and the reduced expression of vimentin and fibronectin proteins was also confirmed by Western blot (FIGS. 3A and 3B). Moreover, we found that BMP7 which functions as an inhibitor of epithelial-mesenchymal transition (EMT) was induced in BJsm cells. Two recent publications have suggested that MET is a critical initiating event during the derivation of induced pluripotent stem cells from mouse fibroblasts (Samavarchi-Tehrani P et al, Cell stem cell; 7(1):64-77; Li R et al, Cell Stem Cell, 7(1):51-63).

We determined that Sp100 functions as a key regulator of cellular maintenance in that its expression in a normal human diploid fibroblast cell line promotes a program of senescence, thus preventing expression of programs for immortalization and malignant transformation. We also showed that expression of the Sp100A isoform synergizes with p53 to activate the $p21^{CIP1}$ promoter and that a shift in the balance between the SAND domain containing isoforms and Sp100A is sufficient to push BJ cells into a senescent state. It is also noteworthy that the Sp100A isoform, which is only known to contain the heterochromatin protein (HP1) binding domain and the Sp100 dimerization domain, is necessary and sufficient to maintain the normal program leading to senescence and thus suppresses transformation in BJ fibroblasts. This implies that chromatin association of Sp100A is required to maintain the normal senescence program by preventing entry into programs that support continued cell division and transformation.

Failure to senesce as a result of the stochastic imbalance of the Sp100A isoform induced by shRNA suppression of all Sp100 isoforms allows a new program to be activated. This new program is facilitated by the transient expression of some stem cell markers and is reversible to some extent. Adding back Sp100A to transformed BJsm cells stops cell division resulting in the death of the transformed cells, likely through the Sp100A mobilization of the extensive amount of sequestered wild-type p53. Thus, Sp100 can function as a tumor suppressor. Since both the SAND and the HMG domains of Sp100 have the potential for sequence specific DNA recognition and may bind to non-methylated CpG sequences in both viral and cellular DNA, we submit, without being bound by theory, that direct DNA binding of the SAND domain containing Sp100 isoforms is involved in gene regulation modified by their potential heterodimerization with Sp100A. Regardless of the mode of recognition, Sp100 proteins regulate endogenous gene expression as they do viral promoters, and thus influence the development of the transformed phenotype. The short time frame required for the emergence of the malignant transformed cells following complete knockdown of Sp100, the high frequency of emergence within a few doubling times, and the reversibility of the high replicative activity by reintroduction of Sp100A are evidence that transformation does not result from the accumulation of multiple heritable genetic mutations in the cell cultures. In summary this data indicate that Sp100 null cells rapidly exhibit a transformed state characterized by activated KRAS, MYC and TERT pathways, cytoplasmic sequestered p53 and pronounced genomic instability. This transformation is preceded by the transient expression of an ESC-like transcription pattern and acquisition of an epithelial phenotype. We show that the loss of expression of a single gene, Sp100, can reprogram the normal differentiation program of human fibroblasts and mimics the reported reprogramming of human fibroblasts by several externally introduced reprogramming factors (Takahashi K et al, 2007 Cell, 131(5):861-72.

Technical and scientific terms used throughout this specification have the same meaning as commonly understood by one of ordinary skill in the art to which this invention belongs and by reference to published texts, which provide one skilled in the art with a general guide to many of the terms used in the present application. Any definitions provided herein are provided for clarity only and are not intended to limit the claimed invention. As used herein, the terms "a" or "an", refers to one or more, for example, "a cell marker" is understood to represent one or more cell markers. As such, the terms "a" (or "an"), "one or more," and "at least one" are used interchangeably herein. As used herein, the term "about" means a variability of 10% from the reference given, unless otherwise specified. While various embodiments in the specification are presented using "comprising" language, under other circumstances, a related embodiment is also intended to be interpreted and described using "consisting of" or "consisting essentially of" language.

Each and every patent, patent application, and publication, including publications listed below, specifically, US Provisional patent application No. 61/585,298 and Negorev D G et al, 2010 Cancer Research, 70(23):9991-10001, and publically available peptide sequences cited throughout the disclosure, is expressly incorporated herein by reference in its entirety. Embodiments and variations of this invention other than those specifically disclosed above may be devised by others skilled in the art without departing from the true spirit and scope of the invention. The appended claims include such embodiments and equivalent variations.

The invention claimed is:

1. A method of producing a composition comprising somatic cells made competent for reprogramming comprising:
- down-regulating or reducing the expression level of all isoforms of Sp100 in selected somatic cells in vitro wherein said selected somatic cells are normal human diploid fibroblasts wherein Sp100 levels are down regulated or reduced by introducing a nucleic acid sequence expressing short hairpin RNA (shRNA) that reduces expression of Sp100;
- serially propagating the cells having reduced Sp100 levels to yield cells with markers of pluripotent stem cells,
- wherein the cells are characterized by increased telomerase activity or telomere length.

2. The method according to claim 1, wherein said markers of pluripotent stem cells are selected from the group consisting of telomerase reverse transcriptase (TERT), LIN28B, SOX2, NANOG and OCT4.

3. An in vitro method for modifying the activity of a somatic cell comprising:
- transitioning a replication limited somatic cell to an immortal cell by reducing the levels of Sp100 expressed in the somatic cells, and serially propagating the cells until the cells demonstrate unrestricted cell growth and increased telomerase activity or telomere length, wherein Sp100 levels are down regulated or reduced by introducing a nucleic acid sequence expressing short hairpin RNA (shRNA) that reduces expression of Sp100
- wherein the somatic cell is a normal human diploid fibroblast.

4. The method according to claim 3, further comprising isolating cells that express markers of pluripotent stem cells.

* * * * *